United States Patent
Nakamura et al.

(10) Patent No.: US 8,609,746 B2
(45) Date of Patent: Dec. 17, 2013

(54) BONE CEMENT COMPOSITION, BONE CEMENT COMPOSITION KIT AND FORMING METHOD OF BONE CEMENT HARDENED MATERIAL

(75) Inventors: Takashi Nakamura, Kyoto (JP); Koji Goto, Kyoto (JP); Takehiro Shibuya, Otsu (JP); Yoshimichi Ueda, Kusatsu (JP); Tokuo Suita, Kusatsu (JP); Masashi Imamura, Kusatsu (JP); Hiroaki Nishii, Kusatsu (JP)

(73) Assignees: Kyoto University, Kyoto (JP); Ishihara Sangyo Kaisha, Ltd., Osaka (JP)

( * ) Notice: Subject to any disclaimer, the term of this patent is extended or adjusted under 35 U.S.C. 154(b) by 189 days.

(21) Appl. No.: 13/203,221

(22) PCT Filed: Feb. 23, 2010

(86) PCT No.: PCT/JP2010/052703
§ 371 (c)(1),
(2), (4) Date: Oct. 3, 2011

(87) PCT Pub. No.: WO2010/098305
PCT Pub. Date: Sep. 2, 2010

(65) Prior Publication Data
US 2012/0035296 A1    Feb. 9, 2012

(30) Foreign Application Priority Data

Feb. 25, 2009  (JP) ................................ 2009-041977
Jun. 15, 2009  (JP) ................................ 2009-142131

(51) Int. Cl.
*A61F 2/28*       (2006.01)
*A61K 6/083*     (2006.01)
*C08L 33/12*     (2006.01)
*C08K 3/22*      (2006.01)

(52) U.S. Cl.
USPC ............ 523/117; 523/116; 525/228; 524/431

(58) Field of Classification Search
USPC .................................. 523/117, 116; 525/228
See application file for complete search history.

(56) References Cited

U.S. PATENT DOCUMENTS

| 6,160,033 | A | 12/2000 | Nies |
| 7,498,363 | B2 | 3/2009 | Bublewitz et al. |
| 2007/0048382 | A1 | 3/2007 | Meyer et al. |
| 2007/0213425 | A1 | 9/2007 | Higham et al. |
| 2009/0239970 | A1* | 9/2009 | Rodrigues et al. ............ 523/117 |
| 2012/0046385 | A1 | 2/2012 | Nakamura et al. |

FOREIGN PATENT DOCUMENTS

| JP | 2000-86419 A | 3/2000 |
| JP | 2000-245821 A | 9/2000 |
| JP | 2000-254220 A | 9/2000 |
| JP | 2001-503290 A | 3/2001 |
| JP | 2004-201869 A | 7/2004 |
| JP | 2007-54369 A | 3/2007 |
| JP | 2007-054619 A | 3/2007 |
| WO | WO 2006/123589 A1 | 11/2006 |
| WO | WO 2007/025633 A2 | 3/2007 |

OTHER PUBLICATIONS

International Search Report dated Apr. 6, 2010 (and English translation thereof) in International Application No. PCT/JP2010/052703.
Yohji Imai et al.: Chracterization of Powder Components of Commercial Bone Cements: Dental Materials Journal: 20(4); 2001: pp. 345-352.
Rodrigues D. C. et al.: Pseudoplasticity and Setting Properties of Two-Solution Bone Cement Containing Poly(methyl methacrylate) Microspheres and Nanospheres for Kyphoplasty and Vertebroplasty: Journal of Biomedical Materials Research: 2009.04; vol. 91B; No. 1; pp. 248-256.

* cited by examiner

*Primary Examiner* — Tae H Yoon
(74) *Attorney, Agent, or Firm* — Holtz Holtz Goodman & Chick, PC

(57) ABSTRACT

A bone cement composition which contains large-diameter (meth)acrylate polymer particles having an average particle diameter of 10 to 60 μm, small-diameter (meth)acrylate polymer particles having an average particle diameter of 0.1 to 2.0 μm, a (meth)acrylate monomer and a polymerization initiator, wherein the content of the small-diameter (meth)acrylate polymer particles is 5 to 30% by mass based on the total mass of the small-diameter (meth)acrylate polymer particles and the large-diameter (meth)acrylate polymer particles, and a part or a whole of the small-diameter (meth)acrylate polymer particles are contained in the form of aggregates having an average particle diameter of 30 to 50 μm.

11 Claims, 3 Drawing Sheets

BONE CEMENT COMPOSITION, BONE CEMENT COMPOSITION KIT AND FORMING METHOD OF BONE CEMENT HARDENED MATERIAL

This application is a U.S. National Phase Application under 35 USC 371 of International Application PCT/JP2010/052703 filed Feb. 23, 2010.

TECHNICAL FIELD

The present invention relates to a bone cement composition, a bone cement composition kit and a production method of a bone cement hardened material.

BACKGROUND ART

A bone cement composition has heretofore been widely used in the world as a bone prosthetic material for a defective part of a bone or an adhesive for fixing a metallic prosthesis such as a hip joint prosthesis to its surrounding bones. A polymethyl methacrylate (PMMA)-based bone cement composition has been most commonly used as such a bone cement composition.

The PMMA-based bone cement composition generally contains polymethyl methacrylate, a methyl methacrylate monomer that is a polymerizable monomer, and a polymerization initiator. The methyl methacrylate monomer is polymerized in the presence of polymethyl methacrylate, whereby the viscosity of the composition is gradually increased to finally form a hardened material.

A PMMA-based bone cement composition heretofore used as the PMMA-based bone cement composition has biocompatibility, but does not have bioactivity, i.e., bone-bonding ability to be bonded to a bone, so that when the composition is used as an adhesive for fixing a prosthesis to its surrounding bones in particular, the adhesive separates from the surrounding bones when a long period of time has elapsed from the application thereof, resulting in causing a problem that looseness occurs between the prosthesis and the bones. In order to solve this problem, in recent years, there has been proposed a composition with titanium dioxide particles added thereto for the purpose of imparting the bioactivity thereto (see, for example, Patent Literature 1).

Such a bone cement composition is generally used by for example, causing a polymerization reaction of the methyl methacrylate monomer to start by kneading it just before its application during a surgical operation or the like and applying the kneaded product to a site to be applied by a handling operation at the time the viscosity of the kneaded product has been increased by the process of leaving the kneaded product to a certain extent.

However, the bone cement composition heretofore used involves a problem that such evils that the kneaded product adheres to, for example, surgical gloves made from a latex, which have been put on hands, during the above-described handling operation in a surgical operation in particular in many cases occur.

Such a problem is caused by the fact that the handling operation is started before the kneaded product of the bone cement composition comes to have a sufficient viscosity, so that it is required to shorten a time necessary for the kneaded product to have a sufficient viscosity required to conduct a good handling operation, said time being called "doughing time". When a filler such as titanium dioxide particles is added to the composition in particular, the above-described problem markedly occurs because the doughing time of such a composition tends to be long, so that it is strongly required to shorten the doughing time.

PRIOR ART LITERATURE

Patent Literature

Patent Literature 1: Japanese Patent Application Laid-Open No. 2007-54619

DISCLOSURE OF THE INVENTION

Technical Problem

The present invention has been made on the basis of the foregoing circumstances and has as its object the provision of a bone cement composition, a bone cement composition kit for obtaining the bone cement composition, and a production method of a bone cement hardened material obtained by setting the bone cement composition, which are short in doughing time that is a time required to become a state in which a good handling operation can be conducted, and are consequently capable of achieving a high working efficiency by shortening the time required before the handling operation is started.

Solution to Problem

A bone cement composition according to the present invention comprises large-diameter (meth)acrylate polymer particles having an average particle diameter of 10 to 60 µm, small-diameter (meth)acrylate polymer particles having an average particle diameter of 0.1 to 2.0 µm, a (meth)acrylate monomer and a polymerization initiator, wherein the content of the small-diameter (meth)acrylate polymer particles is 5 to 30% by mass based on the total mass of the small-diameter (meth)acrylate polymer particles and the large-diameter (meth)acrylate polymer particles.

The bone cement composition according to the present invention may preferably comprise a filler.

In the bone cement composition of such constitution, the filler may preferably contain at least titanium dioxide particles.

The titanium dioxide particles may preferably have a median diameter of 0.5 to 7.0 µm as measured by a laser diffraction/scattering type particle size distribution analyzer and be spherical.

The filler may further contain barium sulfate and/or zirconium oxide.

In bone cement composition according to the present invention, a part or the whole of the small-diameter (meth)acrylate polymer particles may preferably be contained in the form of aggregates having an average particle diameter of 30 to 50 µm.

A bone cement composition kit according to the present invention is a bone cement composition kit for obtaining the above-described bone cement composition and comprises a polymerization initiator-containing kit component containing large-diameter (meth)acrylate polymer particles, small-diameter (meth)acrylate polymer particles and a polymerization initiator, and a monomer-containing kit component containing a (meth)acrylate monomer.

In the bone cement composition kit according to the present invention, the polymerization initiator-containing kit component may preferably contain a filler containing at least titanium dioxide particles.

In the bone cement composition kit according to the present invention, a part or the whole of the small-diameter (meth)acrylate polymer particles may preferably be contained in the form of aggregates having an average particle diameter of 30 to 50 μm.

A production method of a bone cement hardened material according to the present invention comprises a step of kneading a (meth)acrylate monomer and a polymerization initiator in the presence of large-diameter (meth)acrylate polymer particles having an average particle diameter of 10 to 60 μm and small-diameter (meth)acrylate polymer particles having an average particle diameter of 0.1 to 2.0 μm to polymerize the (meth)acrylate monomer, wherein the small-diameter (meth)acrylate polymer particles are used in a proportion of 5 to 30% by mass based on the total mass of the small-diameter (meth)acrylate polymer particles and the large-diameter (meth)acrylate polymer particles.

In the production method of the bone cement hardened material according to the present invention, the (meth)acrylate monomer may preferably be polymerized by going through the process of leaving the kneaded product of the (meth)acrylate monomer and the polymerization initiator to stand.

In the production method of the bone cement hardened material according to the present invention, the kneading of the (meth)acrylate monomer and the polymerization initiator may preferably be conducted in the presence of a filler containing at least titanium dioxide particles together with the large-diameter (meth)acrylate polymer particles and the small-diameter (meth)acrylate polymer particles.

In the production method of the bone cement hardened material according to the present invention, a part or the whole of the small-diameter (meth)acrylate polymer particles may preferably be kneaded in the form of aggregates having an average particle diameter of 30 to 50 μm.

Advantageous Effects of the Invention

According to the bone cement composition of the present invention, the small-diameter (meth)acrylate polymer particles having the specific average particle diameter smaller than that of the large-diameter (meth)acrylate polymer particles are contained in the specific proportion together with the large-diameter particles, whereby the time necessary for the composition to have a sufficient viscosity required to conduct a handling operation is shortened. Therefore, the doughing time that is a time required to become a state in which a good handling operation can be conducted is shortened. As a result, the time required before the handling operation is started can be shortened to achieve a high working efficiency. In particular, such an effect is markedly exhibited when the filler containing titanium dioxide particles is contained. According to the bone cement composition of the present invention, the doughing time tending to require a long time by containing the filler can be shortened, so that the working efficiency can be improved.

According to the bone cement composition kit of the present invention, a bone cement composition can be obtained by subjecting the kit components to a simple kneading treatment, so that a hardened material of the bone cement composition can be easily produced. In addition, the (meth)acrylate monomer and the polymerization initiator are provided as separate kit components, so that the (meth)acrylate monomer can be prevented from being polymerized in a state stored or shipped before application.

According to the production method of the bone cement hardened material of the present invention, a polymerization reaction of the (meth)acrylate monomer for forming the base component in the bone cement formed material to be formed is conducted in the presence of the small-diameter (meth)acrylate polymer particles together with the large-diameter (meth)acrylate polymer particles. Therefore, the reaction is caused to rapidly proceed at an initial stage, and the time necessary for the bone cement composition to have a sufficient viscosity required to conduct a good handling operation is shortened, so that the doughing time that is a time required to become a state in which a good handling operation can be conducted is shortened. As a result, the time required before the handling operation is started can be shortened to achieve a high working efficiency.

MODE FOR CARRYING OUT THE INVENTION

Figure 1:
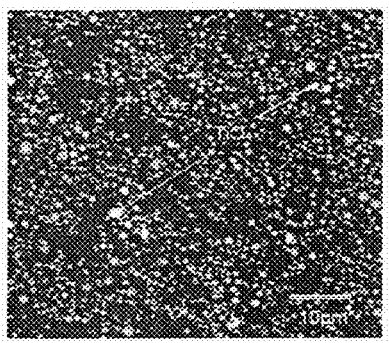
FIG. 1 illustrates an SEM photograph showing a surface (before soaking in a simulated body fluid) of a bone cement hardened material obtained from a composition of Example 13.

The present invention will hereinafter be described in detail.

<Bone Cement Composition>

The bone cement composition according to the present invention contains, as an essential component, small-diameter (meth)acrylate polymer particles having an average particle diameter of 0.1 to 2.0 µm together with a (meth)acrylate monomer, a polymerization initiator and large-diameter (meth)acrylate polymer particles having an average particle diameter of 10 to 60 µm, preferably 20 to 60 µm, and the content of the small-diameter (meth)acrylate polymer particles is 5 to 30% by mass, preferably 5 to 20% by mass based on the total mass of the small-diameter (meth)acrylate polymer particles and the large-diameter (meth)acrylate polymer particles.

This bone cement composition according to the present invention is such that the small-diameter (meth)acrylate polymer particles is contained as a base-forming component together with the (meth)acrylate monomer and the large-diameter (meth)acrylate polymer particles, and the (meth)acrylate monomer that is a polymerizable monomer of the base-forming component is polymerized, whereby the viscosity of the composition is gradually increased, and the composition becomes pasty and finally hardened to form a hardened material.

Here, the hardened material obtained by setting the bone cement composition according to the present invention is such that a base component thereof is formed by a polymer formed by polymerizing the (meth)acrylate monomer, and the large-diameter (meth)acrylate polymer particles and the small-diameter (meth)acrylate polymer particles which make up the base-forming component together with the (meth)acrylate monomer.

(Small-Diameter (Meth)Acrylate Polymer Particles)

The small-diameter (meth)acrylate polymer particles that are essential components of the bone cement composition according to the present invention act as a doughing time adjustor for adjusting and shortening the doughing time that is a time required to become a state in which a good handling operation can be conducted, specifically a state having a sufficient viscosity in the process of setting the bone cement composition.

Here, "doughing time" is defined as a time required until a kneaded product does not adhere to surgical latex gloves from the beginning of kneading in the measuring method "ISO 5833 Annex B" prescribed in ISO standards that are international standards relating to acrylic surgical bone cements.

The small-diameter (meth)acrylate polymer particles are required to have an average particle diameter of 0.1 µm or more and 2.0 µm or less, and the average particle diameter is preferably 0.1 to 1.0 µm, particularly preferably 0.1 to 0.7 µm.

Here, the average particle diameter of the small-diameter (meth)acrylate polymer particles is a median diameter measured by a laser diffraction/scattering type particle size distribution analyzer.

As the laser diffraction/scattering type particle size distribution analyzer, may be specifically used, for example, a particle size distribution measuring instrument "Microtrac" (manufactured by NIKKISO CO., LTD.).

If the average particle diameter of the small-diameter (meth)acrylate polymer particles is too large, the doughing time cannot be practically sufficiently shortened.

The small-diameter (meth)acrylate polymer particles manifest the effect to shorten the doughing time by controlling the average particle diameter thereof to at most 2.0 µm. The doughing time can be specifically controlled within a range of 2.5 to 5 minutes, which is a range practically preferred. However, it is difficult to produce particles having an average particle diameter less than 0.1 µm.

The small-diameter (meth)acrylate polymer particles are obtained by polymerizing a (meth)acrylate monomer as a polymerizable monomer. Specific examples thereof include (A) polyalkyl methacrylates such as polymethyl methacrylate (PMMA), polyethyl methacrylate (PEMA) and polybutyl methacrylate (PBMA) that are polymers of alkyl methacrylate monomers such as methyl methacrylate (MMA), ethyl methacrylate (EMA) and butyl methacrylate, (B) copolymers obtained by copolymerizing methyl methacrylate with at least one monomer selected from the group consisting of styrene, ethyl methacrylate and methyl acrylate, and (C) polymers of dimethacrylate monomers such as bisphenol A diglycidyl dimethacrylate (Bis-GMA), 2,2-bis[4-(3-methacryloxy-2-hydroxypropoxy)phenyl]propane, 2,2-bis(4-methacryloxyethoxyphenyl)propane (Bis-MEPP), triethylene glycol dimethacrylate (TEGDMA), diethylene glycol dimethacrylate (DEGDMA) and ethylene glycol dimethacrylate (EGDMA).

The small-diameter (meth)acrylate polymer particles making up the bone cement composition according to the present invention are preferably those formed of a material that is the same or similar to the large-diameter (meth)acrylate polymer particles making up the base-forming component together. Specifically, such particles are preferably formed of polymethyl methacrylate (PMMA) or a copolymer obtained by using methyl methacrylate as a polymerizable monomer from the relation with the large-diameter (meth)acrylate polymer particles and the (meth)acrylate monomer, and polymethyl methacrylate (PMMA) is particularly preferred.

The small-diameter (meth)acrylate polymer particles are preferably used a polymer having an weight-average molecular weight of, preferably at least 100,000, more preferably 100,000 to 400,000, particularly preferably 150,000 to 400,000.

The weight-average molecular weight of the small-diameter (meth)acrylate polymer particles is controlled within the range of 100,000 to 400,000, whereby the doughing time can be sufficiently shortened, and the resulting hardened material can be provided as that having sufficient mechanical strength.

The reason why the weight-average molecular weight of 150,000 to 400,000 is particularly preferred is as follows. If the weight-average molecular weight of the small-diameter (meth)acrylate polymer particles is less than 150,000, the effect to shorten the doughing time becomes small, so that it is necessary to contain such particles in a higher proportion for sufficiently shortening the doughing time. If the weight-average molecular weight exceeds 400,000 on the other hand, the doughing time can be sufficiently shortened, but there is a possibility that sufficient mechanical strength may not be achieved in the resulting hardened material.

The shape of primary particles of the small-diameter (meth)acrylate polymer particles is preferably spherical.

The shape of the small-diameter (meth)acrylate polymer particles is made spherical, whereby high flowability is imparted to such particles, and uniform dispersibility in the composition is thereby imparted thereto.

Here, the particle shape of the small-diameter (meth)acrylate polymer particles can be confirmed by observing an electron microscope photograph.

The small-diameter (meth)acrylate polymer particles having such a structure can be produced by, for example, subjecting a (meth)acrylate monomer as a polymerizable monomer to a polymerization reaction in an aqueous medium because polymer particles that have a small diameter and are spherical can be easily obtained, or by utilizing, for example, emulsion polymerization or suspension polymerization and subjecting polymer particles obtained by the polymerization reaction to a grinding treatment for the purpose of cracking the polymer particles as needed, and the particles can be specifically produced according to the following publicly known method.

Specific examples of an optimum method for producing the small-diameter (meth)acrylate polymer particles used in the bone cement composition according to the present invention include a method called soap-free polymerization by subjecting a (meth)acrylate monomer as a polymerizable monomer to a polymerization reaction using a redox catalyst composed of potassium persulfate and sodium thiosulfate as a polymerization initiator, and a divalent copper ion compound as a polymerization accelerator under conditions of a polymerization temperature of at least 70° C.

According to this method, the average particle diameter of the resulting (meth)acrylate polymer can be simply controlled within a desired range.

In the bone cement composition according to the present invention, the small-diameter (meth)acrylate polymer particles may be primary particles. However, a part or the whole of the small-diameter (meth)acrylate polymer particles are preferably contained in the form of aggregates.

The average particle diameter of the aggregates of the small-diameter (meth)acrylate polymer particles are preferably 30 to 50 μm, more preferably 30 to 45 μm, particularly preferably 35 to 45 μm.

The shape of the aggregates of the small-diameter (meth)acrylate polymer particles is preferably a spherical form such as true sphere and hemisphere.

The shape of the aggregates is made spherical, whereby high flowability is imparted to such aggregates, and uniform dispersibility in the composition is thereby imparted thereto.

Here, the particle shape of the aggregates of the small-diameter (meth)acrylate polymer particles can be confirmed by observing an electron microscope photograph, and the average particle diameter thereof is a median diameter measured on the base of the electron microscope (SEM) photograph.

As described above, the small-diameter (meth)acrylate polymer particles are contained in the form of aggregates having the specific size, the average particle diameter of which falls within the range of 30 to 50 μm, whereby the size thereof becomes equivalent or approximate to that of the large-diameter (meth)acrylate polymer particles. Thus, when the composition is kneaded, a state high in uniformity can be created, and so the effect to shorten the doughing time is greatly exhibited to achieve an effect that the doughing time can be adjusted to 2.5 to 4 minutes within a more preferable range.

The aggregates of the small-diamter (meth)acrylate polymer particles having such a structure can be produced by a method of providing a dispersion of the small-diameter (meth)acrylate polymer particles and subjecting the dispersion to a spray drying treatment.

Specifically, a spray drying device is used to atomize and eject the dispersion of the small-diameter (meth)acrylate polymer particles as fine misty droplets from a nozzle of the spray drying device into hot air to dry it, thereby obtaining dry granules whose particle shape is spherical.

An ordinary spray drying machine such as an ordinary spray dryer may be used as the spray drying device, and a spray system may be suitably selected from, for example, a disc system, a pressure nozzle system, a two-fluid nozzle system and a four-fluid nozzle system according to the properties of the dispersion of the small-diameter (meth)acrylate polymer particles, the capacity of the spray drying machine, etc.

In the bone cement composition according to the present invention, the content of the small-diameter (meth)acrylate polymer particles is required to be 5% by mass or more and 30% by mass or less based on the total mass of the small-diameter (meth)acrylate polymer particles and the large-diameter (meth)acrylate polymer particles. The content is preferably 5 to 20% by mass, more preferably 10 to 20% by mass, still more preferably 10 to 15% by mass.

If the content of the small-diameter (meth)acrylate polymer particles is too low, the doughing time cannot be shortened to a desired range.

If the content of the small-diameter (meth)acrylate polymer particles is too high on the other hand, the doughing time is more shortened than the desired range, so that it is impossible to conduct a good handling operation. In addition, due to the too high content, the viscosity of the resulting composition is increased or increase in setting temperature is incurred, so that it is impossible to conduct the good handling operation.

Here, the content of the small-diameter (meth)acrylate polymer particles is preferably 0.7 to 23.0% by mass, more preferably 1.5 to 15.0% by mass based on the total mass of the composition. The content is preferably 1.5 to 24.0% by mass, more preferably 2.5 to 15.0% by mass based on the total mass of the base-forming component.

(Large-Diameter (Meth)Acrylate Polymer Particles)

The large-diameter (meth)acrylate polymer particles that are an essential component of the bone cement composition according to the present invention makes up the base-forming component.

The large-diameter (meth)acrylate polymer particles are required to have an average particle diameter of 10 μm or more and 60 μm or less, and the average particle diameter is preferably 20 to 60 μm, more preferably 30 to 50 μm, particularly preferably 35 to 45 μm.

Here, the average particle diameter of the large-diameter (meth)acrylate polymer particles is a median diameter measured by a laser diffraction/scattering type particle size distribution analyzer.

As the laser diffraction/scattering type particle size distribution analyzer, may be specifically used, for example, a particle size distribution measuring instrument "Microtrac" (manufactured by NIKKISO CO., LTD.).

If the average particle diameter of the large-diameter (meth)acrylate polymer particles is too small, the desired doughing time cannot be achieved from the relation with the setting time with the setting time shortened.

If the average particle diameter of the large-diameter (meth)acrylate polymer particles is too large on the other hand, it is necessary to increase of the content of the small-diameter (meth)acrylate polymer particles for achieving the desired doughing time. Increase in setting temperature is incurred by increasing the content of the small-diameter (meth)acrylate polymer particles, so that it is impossible to conduct the good handling operation.

The large-diameter (meth)acrylate polymer particles are obtained by polymerizing a (meth)acrylate monomer as a polymerizable monomer like the small-diameter (meth)acrylate polymer particles. Specific examples thereof include those mentioned as the polymers making up the small-diameter (meth)acrylate polymer particles, such as (A) polyalkyl methacrylates, (B) copolymers obtained by copolymerizing methyl methacrylate with at least one monomer selected from the group consisting of styrene, ethyl methacrylate and methyl acrylate and (C) polymers of dimethacrylate monomers.

The large-diameter (meth)acrylate polymer particles are preferably those obtained by polymerizing the same polymerizable monomer as the (meth)acrylate monomer making up the base-forming component. Specifically, polymethyl methacrylate (PMMA) or a copolymer obtained by using methyl methacrylate as a polymerizable monomer is preferred from the relation with the (meth)acrylate monomer making up the base-forming component, and polymethyl methacrylate (PMMA) is particularly preferred.

The large-diameter (meth)acrylate polymer particles used are preferably formed of a polymer having an weight-average molecular weight of at least 100,000, more preferably 130,000 to 170,000.

The large-diameter (meth)acrylate polymer particles are generally composed of primary particles, and the particle shape thereof is preferably spherical.

The shape of the large-diameter (meth)acrylate polymer particles is made spherical, whereby high flowability is imparted to such particles, and uniform dispersibility in the composition is thereby imparted thereto.

Here, the particle shape of the large-diameter (meth)acrylate polymer particles can be confirmed by observing an electron microscope photograph like the particle shape of the small-diameter (meth)acrylate polymer particles.

The large-diameter (meth)acrylate polymer particles having such a structure can be produced by, for example, subjecting a (meth)acrylate monomer as a polymerizable monomer to a polymerization reaction in an aqueous medium like the small-diameter (meth)acrylate polymer particles, specifically, by utilizing, for example, emulsion polymerization or suspension polymerization and subjecting polymer particles obtained by the polymerization reaction to a cracking treatment as needed.

In the bone cement composition according to the present invention, the content of the large-diameter (meth)acrylate polymer particles is preferably 10 to 70% by mass, more preferably 25 to 70% by mass based on the total mass of the composition. The content is preferably 20 to 75% by mass, more preferably 40 to 75% by mass based on the total mass of the base-forming component.

((Meth)Acrylate Monomer)

The (meth)acrylate monomer that is an essential component of the bone cement composition according to the present invention is that making up the base-forming component. This (meth)acrylate monomer that is a polymerizable monomer is polymerized, whereby the bone cement composition is hardened. As a result, a hardened material is obtained.

Specific examples of the (meth)acrylate monomer include those mentioned as the polymerizable monomers for obtaining the (meth)acrylate polymer making up the base-forming component together with, for example, an alkyl methacrylate monomer or dimethacrylate monomer.

Preferable specific examples of the (meth)acrylate monomer include methyl methacrylate (MMA).

The content of the (meth)acrylate monomer is preferably 19 to 35% by mass, more preferably 24 to 35% by mass based on the total mass of the composition. The content is preferably 20 to 70% by mass, more preferably 25 to 50% by mass based on the total mass of the base-forming component.

(Polymerization Initiator)

As the polymerization initiator that is an essential component of the bone cement composition according to the present invention, may be used, for example, benzoyl peroxide, tert-butyl peroxide, lauroyl peroxide or azobisisobutyronitrile.

Among these, benzoyl peroxide is preferably used because the polymerization reaction of the (meth)acrylate monomer can be caused to rapidly start, and this reaction is easy to be sustained.

The content of the polymerization initiator is preferably 1 to 10 parts by mass, more preferably 2 to 9 parts by mass per 100 parts by mass of the (meth)acrylate monomer.

If the content of the polymerization initiator is too low, there is a possibility that the polymerization reaction of the (meth)acrylate monomer may be hard to proceed. If the content of the polymerization initiator is too high on the other hand, the polymerization initiator is liable to remain in a hardened material formed by polymerizing the (meth)acrylate monomer.

In addition to the base-forming component comprising the small-diameter (meth)acrylate polymer particles, large-diameter (meth)acrylate polymer particles and (meth)acrylate monomer, and the polymerization initiator, which are essential components, a filler is preferably contained in the bone cement composition according to the present invention for the purpose of imparting a function according to use application to the finally obtained hardened material. In addition, a polymerization accelerator is preferably contained together with the polymerization initiator for the purpose of causing the polymerization reaction of the (meth)acrylate monomer to more rapidly proceed.

(Polymerization Accelerator)

As the polymerization accelerator, may be used, for example, N,N-dimethyl-p-toluidine or 2,4,6-tris-(dimethylaminomethyl)phenol.

Among these, N,N-dimethyl-p-toluidine is preferably used because the polymerization reaction of the (meth)acrylate monomer can be caused to rapidly proceed.

The content of the polymerization accelerator is preferably 0.4 to 5.0 parts by mass, more preferably 0.5 to 2.0 parts by mass per 100 parts by mass of the (meth)acrylate monomer.

If the content of the polymerization accelerator is too low, there is a possibility that the polymerization reaction of the (meth)acrylate monomer may be hard to proceed. If the content of the polymerization accelerator is too high on the other hand, the polymerization accelerator is liable to remain in the hardened material formed by polymerizing the (meth)acrylate monomer.

(Filler)

As the filler, may be used one of inorganic substances such as titanium dioxide, calcium phosphate (hydroxyapatite, tricalcium phosphate), barium sulfate, silicon oxide (silica), aluminum oxide (alumina) and zirconium oxide (zirconia), or a mixture of two or more substances thereof suitably selected and combined. Among these, the filler comprising titanium dioxide is preferred.

The reason for it is that since titanium dioxide has apatite-forming ability under an environment of a body fluid, the finally obtained hardened material comes to have high bioactivity by containing the filler comprising titanium dioxide.

As described above, the filler is preferably comprised of titanium dioxide. However, the filler may be a combination of the other inorganic substances, specifically, calcium phosphate (hydroxyapatite, tricalcium phosphate), barium sulfate, silicon oxide (silica), aluminum oxide (alumina) and zirconium oxide (zirconia) with titanium dioxide. Among these, zirconium oxide or barium sulfate having a radiopacifying effect is preferably used in combination.

The content of the filler is preferably at least 5% by mass based on the total mass of the composition.

When the combination of the other inorganic substances with titanium dioxide is used as the filler, their mixing proportions may be suitably set. However, the proportion of titanium dioxide contained in the filler is preferably 5 to 50% by mass, more preferably 5 to 40% by mass, still more preferably 5 to 30% by mass, particularly preferably 10 to 25% by mass based on the mass of the composition.

If the proportion of titanium dioxide contained in the filler is too low, there is a possibility that sufficient bioactivity may not be achieved.

If the proportion of titanium dioxide contained in the filler is too high on the other hand, there is a possibility that the hardened material formed by polymerizing the (meth)acrylate monomer may have low mechanical strength.

When zirconium oxide and/or barium sulfate having a radiopacifying effect is contained in the filler, the proportion thereof is preferably at least 5% by mass, more preferably at least 10% by mass, still more preferably at least 15% by mass based on the total mass of the composition from the viewpoint of radiopacity.

In the bone cement composition according to the present invention, the filler preferably contains at least titanium dioxide particles, and the titanium dioxide particles making up the filler may preferably have a median diameter of 0.5 to 7.0 μm as measured by a laser diffraction/scattering type particle size distribution analyzer. The median diameter is more preferably 1.5 to 7.0 μm, further preferably 2.0 to 7.0 μm, particularly preferably 2.0 to 6.5 μm.

Here, for example, a particle size distribution measuring instrument "LA-950" (manufactured by HORIBA, Ltd.) may be specifically used as the laser diffraction/scattering type particle size distribution analyzer.

If the median diameter of the titanium dioxide particles is too small, there is a possibility that the hardened material formed by polymerizing the (meth)acrylate monomer may have low mechanical strength.

If the median diameter of the titanium dioxide particles is too large on the other hand, the mechanical strength of the hardened material formed by polymerizing the (meth)acrylate monomer becomes too great. Therefore, there is a possibility that such evils that a fracture caused by a great difference in mechanical strength between this hardened material and a bone of an application site of the composition is easy to occur may occur.

In addition, the titanium dioxide particles preferably have a BET specific surface area of 0.5 to 7.0 $m^2/g$ as measured by a nitrogen adsorption method. The BET specific surface area is more preferably 0.5 to 5.0 $m^2/g$, still more preferably 0.5 to 4.0 $m^2/g$, particularly preferably 0.5 to 3.0 $m^2/g$.

Here, for example, a BET specific surface area measuring instrument "MONOSORB" (manufactured by YUASA-IONICS Inc.) may be used in the measurement of the BET specific surface area by the nitrogen adsorption method.

If the BET specific surface area of the titanium dioxide particles is too small, the median diameter thereof becomes large. As a result, the mechanical strength of the hardened material formed by polymerizing the (meth)acrylate monomer becomes too great, so that such evils that a fracture caused by a great difference in mechanical strength between this hardened material and a bone of an application site of the composition is easy to occur come to occur.

If the BET specific surface area of the titanium dioxide particles is too large on the other hand, the mechanical strength (for example, flexural strength) practically required of the hardened material formed by polymerizing the (meth)acrylate monomer is not achieved, which is attributable to the fact that the median diameter thereof becomes too small and the titanium dioxide particles become an aggregated state or porous state.

The titanium dioxide particles making up the bone cement composition according to the present invention are preferably those having a median diameter of 1.5 to 7.0 μm and a BET specific surface area of 0.5 to 5.0 $m^2/g$, more preferably those having a median diameter of 1.5 to 7.0 μm and a BET specific surface area of 0.5 to 4.0 $m^2/g$, still more preferably those having a median diameter of 2.0 to 7.0 μm and a BET specific surface area of 0.5 to 4.0 $m^2/g$, particularly preferably those having a median diameter of 2.0 to 6.5 μm and a BET specific surface area of 0.5 to 3.0 $m^2/g$.

As the titanium dioxide particles, may be used those whose particle form is granular or indeterminate, which are obtained by an ordinary industrial production process, or those having various particle forms publicly known, such as plate, flake, needle, rod, fiber and column forms. However, those having a granular particle form are preferred, and preferable specific examples of the granular form include spherical forms such as true sphere and hemisphere.

The shape of the titanium dioxide particles is made spherical, whereby high flowability is imparted to such particles, and consequently uniform dispersibility in the composition and good filling ability are imparted thereto. As a result, the titanium dioxide particles come to be dispersed in a state high in uniformity in the hardened material formed from this composition, so that it is expected to achieve an effect to inhibit the titanium dioxide particles from separating from this hardened material.

In addition, in the bone cement composition according to the present invention, all the titanium dioxide particles making up the composition preferably have the same form.

Further, the titanium dioxide particles making up the bone cement composition according to the present invention may have any crystal structure of rutile-type, anatase-type and brookite-type and may be amorphous. However, rutile-type titanium dioxide particles are preferred because they have higher apatite-forming ability (bioactivity).

Furthermore, the titanium dioxide particles preferably have hydrophilicity at the surfaces thereof within limits not impairing the affinity for the (meth)acrylate polymer because still higher apatite-forming ability (bioactivity) is achieved.

Examples of a method for imparting still higher hydrophilicity to the surfaces of the titanium dioxide particles include an acid-washing treatment.

Furthermore, the titanium dioxide particles preferably contain little impurities from the viewpoints of safety in a living body, to which the composition is applied, and preventing a prosthesis from being adversely affected. Specifically, the purity of the titanium dioxide particles is preferably at least 99% by mass, more preferably at least 99.5% by mass. On the other hand, the titanium dioxide particles may be subjected to a coating treatment with a small amount of an organic substance such as a silane coupling agent or an inorganic substance such as silica or alumina within limits not impairing the bioactivity and mechanical strength in the composition before use from the viewpoint of the affinity for the (meth)acrylate polymer.

The titanium dioxide particles having such a structure can be produced according to an ordinary method. However, it is optimum to produce the particles according to a method of obtaining titanium dioxide particles by going through the steps of using, for example, titanic acid as a raw material, subjecting a slurry of titanic acid as the raw material to a spray drying treatment after subjected to a wet grinding treatment, as needed, thereby obtaining dried granules, and subjecting the dried granules to a calcinating treatment.

According to this method, the median diameter and the like of the resulting titanium dioxide particles can be simply adjusted to respective desired ranges.

As titanic acid as the raw material of the titanium dioxide particles, may be specifically used orthotitanic acid and metatitanic acid.

Here, orthotitanic acid is a compound obtained by neutralizing an aqueous solution of a titanium compound such as titanium tetrachloride or titanyl sulfate with an alkali in the presence of a seed as needed, also called "titanium hydroxide" and represented by a rational formula of "$Ti(OH)_4$" or "$TiO_2.2H_2O$". Since this orthotitanic acid is amorphous, crystal dislocation is made even at a low heating temperature (calcinating temperature) in the calcinating treatment in such a manner that the resulting titanium dioxide particles have a rutile-type crystal structure. Thus, this acid is preferably used as the raw material.

Metatitanic acid is a compound obtained by thermally hydrolyzing a titanium compound such as titanyl sulfate in an aqueous solution thereof in the presence of a seed as needed, represented by a rational formula of "$TiO(OH)_2$" or "$TiO_2.H_2O$" and having an anatase-type crystal structure.

This titanic acid as the raw material is suspended in a solvent such as, for example, water, thereby preparing a slurry.

The wet grinding treatment, spray drying treatment and calcinating treatment to which the resultant titanic acid slurry is subjected will now be described below in detail.

(1) Wet Grinding Treatment

In this wet grinding treatment, the titanic acid slurry as the raw material is subjected to a grinding treatment, thereby grinding titanic acid in the slurry to obtain a ground titanic acid dispersion in a state that this ground titanic acid has been dispersed in a solvent.

This wet grinding treatment is a preferable treatment because titanic acid in the slurry is dispersed, whereby the median diameter of titanium dioxide particles obtained by going through the spray drying treatment and calcinating treatment of subsequent steps can be adjusted so as to become small.

As a grinding system in this wet grinding treatment, may be used a system that the slurry is caused to pass through an interstice of a rotating circular grindstone by, for example, a colloid mill to apply frictional force and shear force to the slurry to conduct grinding, or a system that the slurry is filled into a cylinder, into which a stirrer has been inserted, together with a spherical medium of rigid beads (for example, hard glass or ceramic) and mixed by, for example, a ball mill, Dyno mill or sand grinder to conduct grinding by high-speed stirring, physical impact by vibration, shear, friction and the like. Another grinding system by a pressure emulsifier type device, high-speed stirring device or the like may also be used.

A rutile dislocation-accelerating seed is preferably mixed in the titanic acid slurry or the ground titanic acid dispersion obtained by the wet grinding treatment.

When the rutile dislocation-accelerating seed is mixed as described above, crystal dislocation for causing the resulting titanium dioxide particles to have a rutile-type crystal structure is easy to occur in the calcinating treatment.

Here, "the rutile dislocation-accelerating seed" is a minute crystal nucleus having a rutile-type crystal structure and serves to accelerate rutile dislocation of titanic acid.

As the rutile dislocation-accelerating seed, may be specifically used, for example, a seed added upon hydrolysis of titanyl sulfate that is a raw material in a method for producing a rutile-type titanium dioxide white pigment by a sulfate process publicly known heretofore.

The amount of the rutile dislocation-accelerating seed mixed may be suitably set. However, the amount is preferably such that a mass ratio (mass of titanium dioxide in titanic acid/mass of titanium dioxide in the rutile dislocation-accelerating seed) to titanium dioxide present in the titanic acid slurry or ground titanic acid dispersion falls within a range of 90/10 to 99/1 because the rutile dislocation can be sufficiently caused.

For example, an ordinary mixing device such as a stirring and mixing machine or mixer may be used in the method for mixing the rutile dislocation-accelerating seed. The mixing of this rutile dislocation-accelerating seed may be conducted before or after the wet grinding treatment, or upon conducting the wet grinding treatment, i.e., at the same time as the wet grinding treatment.

(2) Spray Drying Treatment

In this spray drying treatment, a spray drying device is used to atomize and eject the titanic acid slurry or the ground titanic acid dispersion obtained by the wet grinding treatment conducted as needed as fine misty droplets from a nozzle of the spray drying device into hot air to dry it, thereby obtaining dry granules whose particle form is spherical.

An ordinary spray drying machine such as an ordinary spray dryer may be used as the spray drying device, and a spray system may be suitably selected from, for example, a disc system, a pressure nozzle system, a two-fluid nozzle system and a four-fluid nozzle system according to the properties of the titanic acid slurry or ground titanic acid dispersion, the capacity of the spray drying machine, etc.

The drying conditions (spray drying temperature) of the misty droplets are preferably 150 to 250° C. in intake air temperature and 60 to 120° C. in exhaust air temperature.

In such a spray drying treatment, the median diameter and BET specific surface area of the resulting dry granules can be controlled by, for example, adjusting a titanium dioxide concentration in the titanic acid slurry or ground titanic acid dispersion, adjusting a rotating speed of a disc when the disk system is selected as the spray system of the spray drying machine, or adjusting a spray pressure when the pressure nozzle system, two-fluid nozzle system or four-fluid nozzle system is selected as the spray system of the spray drying machine, thereby controlling the size of sprayed droplets.

In addition, the resulting dry granules can be provided as particles having the same spherical form depending on the spray drying treatment.

(3) Calcinating Treatment

In this calcinating treatment, the dry granules obtained by the spray drying treatment is subjected to a calcinating treatment under higher temperature conditions (specifically, higher than 250° C.) than the spray drying temperature in the spray drying treatment, thereby obtaining calcined particles composed of titanium dioxide.

According to this calcinating treatment, the crystal structure and hardness of the resulting calcined particles can be adjusted together with the median diameter and BET specific surface area of the calcined particles.

With respect to the calcinating conditions of the calcinating treatment, the calcinating temperature is preferably 500 to 1,200° C., more preferably 700 to 1,000° C., particularly preferably 800 to 950° C.

If the calcinating temperature is lower than 500° C., there is a possibility that the crystal dislocation conducted in order for the resulting titanium oxide particles to have a rutile-type crystal structure may be hard to proceed. If the calcinating temperature exceeds 1,200° C. on the other hand, the hardness of the resulting titanium dioxide particles becomes high, so that there is a possibility that abrasion by the titanium dioxide particles may occur on a bone or prosthesis at an application site of the composition.

The calcinating time may be suitable set. However, the time is specifically set to 30 minutes to 10 hours, whereby a sufficient effect by the calcinating, specifically, an effect to accelerate phase dislocation into a rutile type, can be achieved on the calcined particles formed.

No particular limitation is imposed on a calcinating atmosphere. However, an atmosphere, in which oxygen is present, such as the air, is preferred from the economical point of view.

In addition, the calcinating treatment may be such that a first calcinating treatment is conducted at a calcinating temperature of 500 to 800° C., and a second calcinating treatment is then conducted at a calcinating temperature of 800 to 1,200° C. for the purpose of evenly applying a calcinating load.

The calcined particles formed by going through the wet grinding treatment, spray drying treatment and calcinating treatment in this manner may be used as a component of the bone cement composition according to the present invention, i.e., the titanium dioxide particles (filler) making up the bone cement according to the present invention, as they are. However, the calcined particles obtained by the calcinating treatment are preferably subjected to an acid-washing treatment, as needed, for the purpose of imparting still higher hydrophilicity to the surfaces of the particles to achieve still higher apatite-forming ability (bioactivity).

(4) Acid-Washing Treatment

The acid-washing treatment may be conducted by, for example, preparing a slurry of the calcined particles, mixing this slurry with an acid and stirring the resultant mixture at room temperature or under heating. Titanium dioxide particles can be obtained by going through a solid-liquid separation treatment, a washing treatment and a drying treatment, and a cracking treatment conducted as needed after this acid-washing treatment.

Examples of usable acids include inorganic acids such as hydrochloric acid, sulfuric acid, nitric acid and hydrofluoric acid, and organic acids such as acetic acid, citric acid and oxalic acid. The concentration of the acid in the mixture of the slurry and the acid is, for example, 0.01 to 10 mol/L.

When the acid-washing treatment is conducted under heating, the heating is preferably conducted under conditions that the temperature of the mixture of the slurry and the acid is controlled to 30 to 105° C.

This acid-washing treatment is a treatment conducted for imparting still higher hydrophilicity to the surfaces of the titanium dioxide particles as needed and may also be applied to titanium dioxide particles produced by any other process in addition to the calcined particles.

In the course of the production of the titanium dioxide particles, as needed, the calcined particles may be subjected to other steps than such an acid-washing treatment, such as a dry grinding treatment using, for example, a centrifugal grinder or a wet grinding treatment using, for example, a ball mill, Dyno mill or sand grinder for the purpose of deflocculating (cracking) aggregates contained in the calcined particles obtained by the calcinating treatment, a wet classifying treatment by, for example, a stationary method for the purpose of screening out particles having a desired median diameter, and mixing of titanium dioxide particles different in median diameter and/or BET specific surface area from each other.

In addition, the bone cement composition according to the present invention may contain, for example, pigments, antibiotic substances, bone growth factors and other pharmaceutically allowable optional components in addition to the filler and polymerization accelerator.

The bone cement composition of such constitution as described above according to the present invention is applied by for example, causing a polymerization reaction of the methyl methacrylate monomer to start by kneading it just before its application, leaving the kneaded product to stand and applying the kneaded product to a site to be applied by a handling operation at the time the viscosity of the kneaded product has been increased to some extent, thereby forming a hardened material at the application site.

In the bone cement composition according to the present invention, the effect to shorten the doughing time is manifested by containing the small-diameter (meth)acrylate polymer particles having the specific average particle diameter in the specific proportion as the base-forming component, and by this effect, the doughing time as the time necessary for the composition to have a sufficient viscosity required to conduct a good handling operation can be shortened specifically to 2.5 to 5 minutes.

Thus, according to the bone cement composition of the present invention, the doughing time can be shortened, so that the time required before the handling operation is started can be shortened to achieve a high working efficiency.

In addition, the bone cement composition according to the present invention tends to slow a setting time to some extent in addition to the fact that the doughing time can be shortened, so that there is a possibility that workability may be improved attending on the fact that the time up to setting through the doughing time, i.e., the working time, becomes long.

In the bone cement composition according to the present invention, the filler containing at least the titanium dioxide particles is contained, whereby the apatite-forming ability under an environment of a body fluid that is possessed by the titanium dioxide particles themselves is manifested, so that excellent bioactivity is achieved.

In addition, the titanium dioxide particles making up the filler is formed so as to have the specific size, whereby good strength according to use applications is exhibited, so that high mechanical strength can be achieved.

When the filler containing at least the titanium dioxide particles is contained as described above, the effect that the doughing time can be shortened is markedly exhibited, and so the doughing time tending to require a long time by adding the filler can be shortened, so that the working efficiency can be improved.

The bone cement composition according to the present invention is such that the high working efficiency can be achieved by shortening the doughing time, so that the composition can be suitably used as a prosthetic material for a defective part of a bone, an adhesive for fixing a metallic prosthesis such as a hip joint prosthesis to its surrounding bones or a fixing agent for prostheses in a situation that an operation such as a surgical operation in particular is preferably conducted for a time as short as possible, and besides, can also be used as an artificial bone-forming material for forming an artificial bone. In addition, in the composition, in which the filler containing at least the titanium dioxide particles is contained, the bioactivity is achieved, and moreover the high mechanical strength is achieved, so that such a composition is more suitable for use as a prosthetic material for a defective part of a bone, an adhesive for fixing a prosthesis to its surrounding bones, a fixing agent for prostheses and an artificial bone-forming material.

Such a bone cement composition according to the present invention can be produced by mixing the base-forming component comprising the small-diameter (meth)acrylate polymer particles, the large-diameter (meth)acrylate polymer particles and the (meth)acrylate monomer, and the polymerization initiator, which are essential components, and other optional components. The composition may also be prepared as needed by, for example, containing the individual components in separate storage members in advance to store them as a kit from the viewpoint of simplicity and convenience of its production.

<Bone Cement Composition Kit>

The bone cement composition kit according to the present invention is a bone cement composition kit for obtaining the bone cement composition according to the present invention.

This bone cement composition kit according to the present invention comprises a monomer-containing kit component containing at least the (meth)acrylate monomer among the small-diameter (meth)acrylate polymer particles, the large-diameter (meth)acrylate polymer particles, the (meth)acrylate monomer and the polymerization initiator, which are essential components of the bone cement composition according to the present invention to be formed, and a polymerization initiator-containing kit component containing at least the polymerization initiator.

Such a bone cement composition kit according to the present invention only requires to provide the (meth)acrylate monomer and the polymerization initiator as separate kit components from the viewpoint of preventing the (meth) acrylate monomer from undergoing a polymerization reaction before application. For example, the individual components of the bone cement composition to be formed may be provided as separate kit components. However, the kit is preferably composed of two kit components of a monomer-containing kit component and a polymerization initiator-containing kit component from the viewpoints of convenience of carrying the bone cement composition kit and simplicity of a polymerization reaction operation.

In the bone cement composition kit composed of the two kit components of the monomer-containing kit component and the polymerization initiator-containing kit component, the small-diameter (meth)acrylate polymer particles, the large-diameter (meth)acrylate polymer particles and the polymerization initiator among the essential components of the bone cement composition to be formed are generally solid, and the (meth)acrylate monomer is generally liquid, so that it is preferable that only the (meth)acrylate monomer is contained in the monomer-containing kit component, and the small-diameter (meth)acrylate polymer particles and the large-diameter (meth)acrylate polymer particles are contained in the polymerization initiator-containing kit component together with the polymerization initiator. A part or the whole of the small-diameter (meth)acrylate polymer particles are preferably contained in the form of aggregates having an average particle diameter of 30 to 50 μm.

When the bone cement composition obtained from the bone cement composition kit according to the present invention contains the filler containing at least the titanium dioxide particles and/or the polymerization accelerator together with the essential components, specifically, the small-diameter (meth)acrylate polymer particles, the large-diameter (meth) acrylate polymer particles, the (meth)acrylate monomer and the polymerization initiator, these filler and/or polymerization accelerator may be provided as separate kit components from the monomer-containing kit component and the polymerization initiator-containing kit component. However, these components are preferably contained in any one of these two kit components from the viewpoints of convenience of carrying the kit and simplicity of a polymerization reaction operation.

Specifically, the filler is generally in a solid state and is thus preferably contained in the polymerization initiator-containing kit component of the two kit components. On the other hand, the polymerization accelerator is generally in a liquid state and does not have reactivity to the (meth)acrylate monomer, so that the accelerator is preferably contained in the monomer-containing kit component of the two kit components.

As storage members for storing the kit components of the bone cement composition kit, any members may be used so far as they can store and carry the respective kit components. For example, glass, metal or plastic containers, or packaging members made of, for example, paper or plastics may be suitably selected for use.

According to such a bone cement composition kit of the present invention, a bone cement composition can be obtained by subjecting the kit components to a simple kneading treatment, so that a bone cement hardened material can be easily produced. In addition, the (meth)acrylate monomer and the polymerization initiator are provided as separate kit components, so that the (meth)acrylate monomer can be prevented from being polymerized in a state stored or shipped before application.

When the bone cement composition kid according to the present invention is composed of the 2 kit components of the monomer-containing kit component and the polymerization initiator-containing kit component, the total number of kit components is small, so that the convenience of carrying the bone cement composition kit and the simplicity of the polymerization reaction operation are excellently achieved.

<Production Method of Bone Cement Hardened Material>

The production method of a bone cement hardened material according to the present invention comprises a step of kneading a (meth)acrylate monomer and a polymerization initiator in the presence of large-diameter (meth)acrylate polymer particles having an average particle diameter of 10 to 60 μm, preferably 20 to 60 μm and small-diameter (meth) acrylate polymer particles having an average particle diameter of 0.1 to 2.0 μm to polymerize the (meth)acrylate monomer, wherein the small-diameter (meth)acrylate polymer particles are used in a proportion of 5 to 30% by mass, preferably 5 to 20% by mass, more preferably 10 to 20% by mass, particularly preferably 10 to 15% by mass based on the total mass of the small-diameter (meth)acrylate polymer particles and the large-diameter (meth)acrylate polymer particles.

In other words, the production method of the bone cement hardened material according to the present invention intends to obtain a hardened material formed by using the bone cement composition according to the present invention as a material and polymerizing the (meth)acrylate monomer making up the base-forming component of the bone cement composition.

In such a production method of the bone cement hardened material according to the present invention, a part or the whole of the small-diameter (meth)acrylate polymer particles are preferably used in the form of aggregates having an average particle diameter of 30 to 50 μm. In addition, the mixing of the (meth)acrylate monomer and the polymerization initiator and the polymerization of the (meth)acrylate monomer are preferably conducted in the presence of a filler containing at least titanium dioxide particles together with the large-diameter (meth)acrylate polymer particles and the small-diameter (meth)acrylate polymer particles.

Specifically, according to this production method of the hardened material of the present invention, the (meth)acrylate monomer is first added into a container charged with the large-diameter (meth)acrylate polymer particles, the small-diameter (meth)acrylate polymer particles and the polymerization initiator, and optionally with the filler such as titanium dioxide particles to knead the contents, thereby bringing the (meth)acrylate monomer into contact with the polymerization initiator to start a polymerization reaction of the (meth) acrylate monomer. The kneaded product is left to stand, thereby causing the polymerization reaction of the (meth) acrylate monomer to proceed.

The polymerization accelerator may also be used, as needed, in the reaction system of the polymerization reaction of the (meth)acrylate monomer.

Here, the kneading conditions vary according to the respective kinds and used amounts of the large-diameter (meth)acrylate polymer particles, the small-diameter (meth) acrylate polymer particles, the (meth)acrylate monomer and the polymerization initiator. However, for example, the kneading time is about 1.5 minutes under a degassed atmosphere formed by using a closed container or the like capable of degassing under vacuum.

The kneaded product is then caused to pass through the process of leaving it to stand. In short, a handling operation for applying the kneaded product to an application site is conducted at the time its viscosity has been increased to some extent by passing through the doughing time, thereby forming a bone cement hardened material at the application site.

Specific examples of the handling operation include a method of applying the kneaded product, whose viscosity has been increased to some extent, to the application site by a manual work and a method of injecting the kneaded product by means of an injector. As the injector, may be used various tools and instruments, for example, a syringe, a dispenser, a plunger, and the so-called cement gun equipped with an ejection orifice.

Here, the bone cement hardened material obtained in this manner exhibits its function by setting the bone cement composition applied to the application site as, for example, a prosthetic material for a defective part of a bone, an adhesive for fixing a metallic prosthesis such as a hip joint prosthesis to its surrounding bones or a fixing agent for the prosthesis at the application site.

According to such a production method of the bone cement hardened material of the present invention, the polymerization reaction of the (meth)acrylate monomer for forming the base component in the bone cement hardened material to be formed is conducted in the presence of the large-diameter (meth)acrylate polymer particles and the small-diameter (meth)acrylate polymer particles, whereby the doughing time that is a time necessary for the composition to have a sufficient viscosity required to conduct a good handling operation can be shortened to about 2.5 to 5 minutes or about 2.5 to 4 minutes when the small-diameter (meth)acrylate polymer particles are used in the form of aggregates, by the action of the small-diameter (meth)acrylate polymer.

Here, in the production method of the bone cement hardened material of the present invention, the time necessary for the kneading and the doughing time become to about 1.5 minutes and within 5 minutes, respectively, and the setting time necessary for the setting from the beginning of the kneading becomes about 10 minutes, so that the working time that is a time up to the setting from after the passage of the doughing time can be sufficiently ensured because the time required to apply the kneaded product to the application site by the ordinary handling operation is about 3 minutes.

In addition, an artificial bone can also be obtained by the production method of the bone cement hardened material according to the present invention in the following manner.

Namely, a kneaded product of, for example, the large-diameter (meth)acrylate polymer particles, the small-diameter (meth)acrylate polymer particles, the polymerization initiator and the (meth)acrylate monomer, and the filler such as titanium dioxide particles and/or the polymerization accelerator, which are added as needed, is obtained, this kneaded product is put in a releasable container having a desired shape after the doughing time has elapsed, and left at rest and hardened in that state, thereby forming it. A formed material having a shape conforming to the shape of the container can be thereby obtained as an artificial bone.

In the production method of the bone cement hardened material as such an artificial bone, the production conditions vary according to the respective kinds and used amounts of the titanium dioxide particles, the (meth)acrylate polymers, the (meth)acrylate monomer and the polymerization initiator, the shape of the formed material to be formed, and the like. However, as the kneading conditions, the kneading time is about 1.5 minutes under, for example, a degassed atmosphere, and the doughing time is within a range of 2.5 to 5 minutes, and as the standing conditions, the standing time is at least 24 hours under, for example, an environment of 30° C. in temperature.

EXAMPLES

Examples of the present invention will hereinafter be specifically described. However, the present invention is not limited to these Examples.

Methods for measurements of the average particle diameters of large-diameter (meth)acrylate polymer particles, the average particle diameters (primary particle diameters) of small-diameter (meth)acrylate polymer particles, and the average particle diameter of aggregates of small-diameter (meth)acrylate polymer particles, which were conducted in the following Examples and Comparative Examples, are as follows.

(Measuring Method of Average Particle Diameters of Large-Diameter and Small-Diameter (Meth)Acrylate Polymer Particles)

As an average particle diameter of each particle sample, a median diameter measured by a laser diffraction/scattering type particle size distribution analyzer was measured, and a particle size distribution measuring instrument "Microtrac" (manufactured by NIKKISO CO., LTD.) was used as the laser diffraction/scattering type particle size distribution analyzer.

More specifically, powder particles, the average particle diameter of which was to be measured, were added into 50 mL of a dispersion medium composed of an aqueous solution of Tween 20 (polyoxyethylene (20) sorbitan monolaurate, product of KANTO CHEMICAL CO., INC.) having a concentration of 0.2% by mass, and the resultant mixture was stirred and mixed, thereby preparing a suspension. This suspension was poured from a sample inlet port into the particle size distribution measuring instrument "Microtrac" (manufactured by NIKKISO CO., LTD.) and subjected to an ultrasonic treatment for 3 minutes, and the measurement was then started.

(Measuring Method of Average Particle Diameter of Aggregates of Small-Diameter (Meth)Acrylate Polymer Particles)

As an average particle diameter of each aggregate sample, a median diameter calculated on the basis of an electron microscope (SEM) photograph was measured.

More specifically, a field emission type scanning electron microscope "S-4800 Model" (manufactured by Hitachi High-Technologies Corporation) was used to conduct the measurement under conditions of an accelerating voltage of 1.5 kV, no vapor deposition on a surface and an objective magnification of 200 times.

Methods for measurements of the median diameters and BET specific surface areas of titanium dioxide particles, and titanium dioxide concentrations, which were conducted upon the preparation of the titanium dioxide particles together with the preparation method of the titanium dioxide particles used in the following Examples and Comparative Examples, are as follows.

(Measuring Method of Median Diameter of Titanium Dioxide Particles)

The median diameter was measured by a laser diffraction/scattering type particle size distribution analyzer, and the measurement was conducted by using a particle size distribution measuring instrument "LA-950" (manufactured by HORIBA, Ltd.) as the laser diffraction/scattering type particle size distribution analyzer.

More specifically, powder particles, the median diameter of which was to be measured, were added into 50 mL of a dispersion medium composed of an aqueous sodium hexametaphosphate solution having a concentration of 0.2% by mass, and the resultant mixture was stirred and mixed, thereby preparing a suspension. This suspension was poured from a sample inlet port into the particle size distribution measuring instrument "LA-950" (manufactured by HORIBA, Ltd.) and subjected to an ultrasonic treatment for 3 minutes, and the measurement was then started.

(Measuring Method of Bet Specific Surface Area of Titanium Dioxide Particles)

The BET specific surface area was measured by a nitrogen adsorption method, and the measurement was conducted by using a BET specific surface area measuring instrument "MONOSORB" (manufactured by YUASA-IONICS Inc.).

This BET specific surface area measuring instrument "MONOSORB" (manufactured by YUASA-IONICS Inc.) is suitable for the measurement by the BET single point method.

(Measuring Method of Titanium Dioxide Concentration)

The titanium dioxide concentration, specifically, the titanium dioxide concentrations in an orthotitanic acid slurry and a rutile dislocation-accelerating seed slurry were measured by taking each slurry in a crucible to dry it and then subjecting it to a calcinating treatment under conditions of 750° C. in temperature.

Preparation Example 1 of Titanium Dioxide Particles

Preparation of Titanic Acid Slurry

After an aqueous titanium tetrachloride solution was neutralized with aqueous ammonia, filtration and water washing were conducted, thereby obtaining orthotitanic acid in a wet cake state. Thereafter, the resultant orthotitanic acid in the wet cake state and pure water were charged into a mixer and sufficiently stirred and mixed, thereby obtaining an orthotitanic acid slurry.

(Wet Grinding Process)

A Dyno mill "DYNO-MILL" (manufactured by SHIN-MARU ENTERPRISES CORPORATION) was used to charge 480 mL of titania beads (product of Toyama Ceramics Co., Ltd.) having an average particle diameter of 0.6 mm into the interior (volume: about 600 mL) of this Dyno mill body, and the above-obtained orthotitanic acid slurry was fed under conditions of a flow rate of 160 mL/min and treated in the Dyno mill by rotating a rotor blade provided in the interior of the mill body, thereby obtaining an orthotitanic acid slurry (hereinafter also referred to as "the grinding treatment-subjected titanic acid slurry").

The concentration of titanium dioxide in this grinding treatment-subjected titanic acid slurry was 10.39% by mass.

(Spray Drying Process)

A rutile dislocation-accelerating seed slurry having a titanium dioxide concentration of 19.98% by mass was first mixed with the grinding treatment-subjected titanic acid slurry obtained in Wet grinding process in a proportion that a mass ratio (mass of titanium dioxide in titanic acid/mass of titanium dioxide in the rutile dislocation-accelerating seed) to titanium dioxide present in the grinding treatment-subjected titanic acid slurry is 95/5, and the concentration of titanium dioxide in this mixture was adjusted to 5.0% by mass by adding pure water thereto, thereby preparing a mixed slurry. After the resultant mixed slurry was stirred and mixed by means of a domestic mixer, coarse particles were removed by a 200-mesh sieve, thereby obtaining a slurry for spray drying treatment (hereinafter also referred to as "the slurry for spray drying treatment").

A spray drying machine "MDL-050C" (manufactured by Fujisaki Electric Co., Ltd.) was then used, and the slurry for spray drying treatment was fed to this spray drying machine by a roller pump to conduct a spray drying treatment under conditions of a roller pump flow rate of 25 mL/min (set flow rate when pure water was fed), an intake air temperature of 200° C., an exhaust air temperature of 65 to 85° C. and an air flow rate of 80 L/min. In a powder collecting part provided in the spray drying machine and comprises a glass container and a bag filter, portions large in median diameter and portions small in median diameter of the dried granules obtained by this spray drying treatment were collected in the glass container and the bag filter, respectively.

Here, the portions collected in the glass container of the spray drying machine are called "cyclone product", and the portions collected in the bag filter are called "bag product" on the other hand.

(Calcinating Process)

Those collected as the cyclone product of the dried granules obtained in Spray drying process were put in a calcinating crucible to conduct a calcinating treatment by means of an electric furnace "SK-3035F" (manufactured by MOTOYAMA CO., LTD.) under calcinating conditions of a calcinatingcalcinating temperature of 850° C. (heating rate: 10° C./min) and a calcinating time of 6 hours, and air cooling was then conducted, thereby obtaining calcined particles.

(Wet Grinding Process)

A pot mill (volume: 0.87 L) was first charged with 200 g of the calcined particles obtained in Calcinating process, 350 mL of titania beads (product of Toyama Ceramics Co., Ltd.) having an average particle diameter of 0.6 mm and 350 mL of pure water, and the calcined particles were subjected to a rotational treatment for 6 hours by means of a pot mill rotating table "ANZ-51S" (manufactured by NITTO KAGAKU Co., Ltd.), thereby obtaining a titanium dioxide slurry with the calcined particles ground and dispersed therein.

After the resultant titanium dioxide slurry was then put in a glass beaker, pure water was poured in such a manner that the total liquid quantity amounts to 3 L to conduct a spontaneous sedimentation treatment overnight. Thereafter, a supernatant was removed by suction, a proper amount of pure water was added to the residue, and dispersing treatment was then conducted by means of an ultrasonic washing machine, thereby obtaining a titanium dioxide slurry for being subjected to an acid-washing treatment.

(Acid-Washing Process)

Hydrochloric acid was added to the titanium dioxide slurry obtained in Wet grinding process so as to give a concentration of 1 normal, and the resultant mixture was stirred for 3 hours at room temperature by means of a stirring motor, thereby conducting an acid-washing treatment. Thereafter, a supernatant was removed by decantation, and the residue was filtered and washed with pure water by means of a Buchner funnel to confirm that the specific resistance of a filtrate is at least 10 kΩ.m. Thereafter, a washed cake was collected and subjected to a drying treatment under conditions of a temperature of 110° C. by means of a constant-temperature drying machine and to a dry grinding treatment by means of a centrifugal grinder "ZM100" (manufactured by NIHONSEIKI KAISHA LTD.), in which a mesh having a screen diameter of 1.5 mm had been set, under conditions of a rotating speed of 14,000 rpm, thereby obtaining titanium dioxide particles (hereinafter also referred to as "titanium dioxide particles (a)") having a median diameter of 2.7 μm and a BET specific surface area of 1.95 m$^2$/g.

From a result of powder X-ray diffraction using a powder X-ray diffractometer "RINT 1200" (manufactured by Rigaku Corporation), it was confirmed that the titanium dioxide particles (a) are rutile-type titanium dioxide particles, and from a result of observation through a scanning electron microscope "S-3200N" (manufactured by Hitachi, Ltd.), it was confirmed that the shape thereof is spherical.

Preparation Example 2 of Titanium Dioxide Particles

Titanium dioxide particles (hereinafter also referred to as "titanium dioxide particles (b)") having a median diameter of 3.1 μm and a BET specific surface area of 2.1 m$^2$/g were obtained in the same manner as in Preparation Example 1 of titanium dioxide particles.

From a result of powder X-ray diffraction using the powder X-ray diffractometer "RINT 1200" (manufactured by Rigaku Corporation), it was confirmed that the titanium dioxide particles (b) are rutile-type titanium dioxide particles, and from a result of observation through the scanning electron microscope "S-3200N" (manufactured by Hitachi, Ltd.), it was confirmed that the shape thereof is spherical.

Preparation Example 3 of Titanium Dioxide Particles

Titanium dioxide particles (hereinafter also referred to as "titanium dioxide particles (c)") having a median diameter of 2.9 μm and a BET specific surface area of 2.5 m$^2$/g were obtained in the same manner as in Preparation Example 1 of titanium dioxide particles.

From a result of powder X-ray diffraction using the powder X-ray diffractometer "RINT 1200" (manufactured by Rigaku Corporation), it was confirmed that the titanium dioxide particles (c) are rutile-type titanium dioxide particles, and from a result of observation through the scanning electron microscope "S-3200N" (manufactured by Hitachi, Ltd.), it was confirmed that the shape thereof is spherical.

Example 1

A mixed powder component was obtained by mixing 44.885% by mass of polymethyl methacrylate powder (average particle diameter: 39.77 μm, weight-average molecular weight: 167,000, particle shape: spherical; product of SEKISUI PLASTICS CO., LTD.) as large-diameter (meth)acrylate polymer particles, 6.707% by mass of polymethyl methacrylate powder (average particle diameter: 0.5 μm, average molecular weight: 190,000, particle shape: spherical; product of SEKISUI PLASTICS CO., LTD.) as small-diameter (meth)acrylate polymer particles, 19.654% by mass of the titanium dioxide particles (a) as a filler and 1.474% by mass of benzoyl peroxide (product of KAWAGUCHI CHEMICAL CO., LTD.) as a polymerization initiator.

On the other hand, a mixed liquid component was obtained by adding and mixing 0.256% by mass of N,N-dimethyl-p-toluidine (product of Mitsuboshi Chemical Co., Ltd.) as a polymerization accelerator with 27.024% by mass of methyl methacrylate (product of Wako Pure Chemical Industries, Ltd.) as a (meth)acrylate monomer.

The resultant mixed powder component and mixed liquid component were stored in separate containers, thereby preparing a bone cement composition kit (hereinafter also referred to as "the bone cement composition kit (1)") made up of a polymerization initiator-containing kit component composed of the mixed powder component and a monomer-containing kit component composed of the mixed liquid component.

In this bone cement composition kit (1), the content of the large-diameter (meth)acrylate polymer particles was 57.094% by mass based on the total mass of the base-forming component, and the content of the small-diameter (meth)acrylate polymer particles was 13.0% by mass based on the total mass of the small-diameter (meth)acrylate polymer particles and the large-diameter (meth)acrylate polymer particles.

The proportion of the polymerization initiator to the (meth)acrylate monomer was 5.454% by mass, and the proportion of the polymerization accelerator to the (meth)acrylate monomer was 0.947% by mass.

After the polymerization initiator-containing kit component of the bone cement composition kit (1) was put in a kneading container made of polytetrafluoro-ethylene, the monomer-containing kit component of the bone cement composition kit (1) was poured therein, thereby obtaining a bone cement composition.

This bone cement composition was kneaded for 30 seconds according to a measuring method based on ISO 5833 and then further kneaded for 1 minute under a degassed atmosphere. The resultant kneaded product was then handled by hands worn with powder-free surgical latex gloves to measure a time necessary for the kneaded product to become a state causing no adhesion to the surgical gloves, thereby confirming its doughing time. A result is shown in Table 1.

The kneaded product, the doughing time of which had been confirmed, was cast in a polytetrafluoroethylene-made mold equipped with thermocouple wires having an outer diameter of 0.5 mm to calculate out a setting time based on a maximum temperature confirmed by measuring the temperature of the kneaded product every 5 seconds by this thermocouple wires. A result is shown in Table 1.

Example 2

A bone cement composition kit (hereinafter also referred to as "the bone cement composition kit (2)") was prepared in the same manner as in Example 1 except that polymethyl methacrylate powder (product of SEKISUI PLASTICS CO., LTD.), whose average particle diameter was 33.93 μm, whose weight-average molecular weight was 141,000, and whose particle shape was spherical, was used as the large-diameter (meth)acrylate polymer particles in Example 1, and the used amounts of the large-diameter (meth)acrylate polymer particles and the small-diameter (meth)acrylate polymer particles were changed to 45.401% by mass and 6.191% by mass, respectively.

In this bone cement composition kit (2), the content of the large-diameter (meth)acrylate polymer particles was 57.750% by mass based on the total mass of the base-forming component, and the content of the small-diameter (meth)acrylate polymer particles was 12.0% by mass based on the total mass of the small-diameter (meth)acrylate polymer particles and the large-diameter (meth)acrylate polymer particles.

The proportion of the polymerization initiator to the (meth)acrylate monomer was 5.454% by mass, and the proportion of the polymerization accelerator to the (meth)acrylate monomer was 0.947% by mass.

With respect to the resultant bone cement composition kit (2), the doughing time was confirmed and the setting time was calculated out, by the same method as in Example 1. The results are shown in Table 1.

Example 3

A bone cement composition kit (hereinafter also referred to as "the bone cement composition kit (3)") was prepared in the same manner as in Example 1 except that the small-diameter (meth)acrylate polymer particles in Example 1 were changed to aggregates (particle shape: spherical) having an average particle diameter of 40 µm by means of a spray drying machine before use.

With respect to the resultant bone cement composition kit (3), the doughing time was confirmed and the setting time was calculated out, by the same method as in Example 1. The results are shown in Table 1.

Example 4

A bone cement composition kit (hereinafter also referred to as "the bone cement composition kit (4)") was prepared in the same manner as in Example 2 except that the small-diameter (meth)acrylate polymer particles in Example 2 were changed to aggregates (particle shape: spherical) having an average particle diameter of 40 µm by means of a spray drying machine before use.

With respect to the resultant bone cement composition kit (4), the doughing time was confirmed and the setting time was calculated out, by the same method as in Example 1. The results are shown in Table 1.

Example 5

A bone cement composition kit (hereinafter also referred to as "the bone cement composition kit (5)") was prepared in the same manner as in Example 1 except that polymethyl methacrylate powder (product of SEKISUI PLASTICS CO., LTD.), whose average particle diameter was 45.58 µm, whose weight-average molecular weight was 141,000, and whose particle shape was spherical, was used as the large-diameter (meth)acrylate polymer particles in Example 1, and the used amounts of the large-diameter (meth)acrylate polymer particles and the small-diameter (meth)acrylate polymer particles were changed to 44.369% by mass and 7.223% by mass, respectively.

In this bone cement composition kit (5), the content of the large-diameter (meth)acrylate polymer particles was 56.438% by mass based on the total mass of the base-forming component, and the content of the small-diameter (meth)acrylate polymer particles was 14.0% by mass based on the total mass of the small-diameter (meth)acrylate polymer particles and the large-diameter (meth)acrylate polymer particles.

With respect to the resultant bone cement composition kit (5), the doughing time was confirmed and the setting time was calculated out, by the same method as in Example 1. The results are shown in Table 1.

Example 6

A bone cement composition kit (hereinafter also referred to as "the bone cement composition kit (6)") was prepared in the same manner as in Example 5 except that the small-diameter (meth)acrylate polymer particles in Example 5 were changed to aggregates (particle shape: spherical) having an average particle diameter of 40 µm by means of a spray drying machine before use.

With respect to the resultant bone cement composition kit (6), the doughing time was confirmed and the setting time was calculated out, by the same method as in Example 1. The results are shown in Table 1.

Example 7

A bone cement composition kit (hereinafter also referred to as "the bone cement composition kit (7)") was prepared in the same manner as in Example 1 except that polymethyl methacrylate powder (product of SEKISUI PLASTICS CO., LTD.), whose average particle diameter was 31.11 µm, whose weight-average molecular weight was 148,900, and whose particle shape was spherical, was used as the large-diameter (meth)acrylate polymer particles in Example 1, the used amounts of the large-diameter (meth)acrylate polymer particles and the small-diameter (meth)acrylate polymer particles were changed to 30.059% by mass and 5.305% by mass, respectively, the small-diameter (meth)acrylate polymer particles were changed to aggregates (particle shape: spherical) having an average particle diameter of 40 µm by means of a spray drying machine before use, the titanium dioxide particles (b) were used as the filler in place of the titanium dioxide particles (a), the used amount thereof was changed to 39.293% by mass, the used amount of benzoyl peroxide was changed to 1.473% by mass, the used amount of methyl methacrylate was changed to 23.575% by mass, and the used amount of N,N-dimethyl-p-toluidine was changed to 0.295% by mass.

In this bone cement composition kit (7), the content of the large-diameter (meth)acrylate polymer particles was 51.000% by mass based on the total mass of the base-forming component, and the content of the small-diameter (meth)acrylate polymer particles was 15.0% by mass based on the total mass of the small-diameter (meth)acrylate polymer particles and the large-diameter (meth)acrylate polymer particles.

The proportion of the polymerization initiator to the (meth)acrylate monomer was 6.248% by mass, and the proportion of the polymerization accelerator to the (meth)acrylate monomer was 1.251% by mass.

With respect to the resultant bone cement composition kit (7), the doughing time was confirmed and the setting time was calculated out, by the same method as in Example 1. The results are shown in Table 1.

Example 8

A bone cement composition kit (hereinafter also referred to as "the bone cement composition kit (8)") was prepared in the same manner as in Example 1 except that polymethyl methacrylate powder (product of SEKISUI PLASTICS CO., LTD.), whose average particle diameter was 12.93 µm, whose weight-average molecular weight was 139,600, and whose particle shape was spherical, was used as the large-diameter (meth)acrylate polymer particles in Example 1, the used amounts of the large-diameter (meth)acrylate polymer particles and the small-diameter (meth)acrylate polymer particles were changed to 23.575% by mass and 5.894% by mass, respectively, the small-diameter (meth)acrylate polymer particles were changed to aggregates (particle shape: spherical) having an average particle diameter of 40 µm by means of a spray drying machine before use, the titanium dioxide particles (b) were used as the filler in place of the titanium dioxide particles (a), the used amount thereof was changed to 39.293% by mass, the used amount of benzoyl peroxide was changed to 1.473% by mass, the used amount of methyl methacrylate was changed to 29.470% by mass, and the used amount of N,N-dimethyl-p-toluidine was changed to 0.295% by mass.

In this bone cement composition kit (8), the content of the large-diameter (meth)acrylate polymer particles was 39.999% by mass based on the total mass of the base-forming component, and the content of the small-diameter (meth)acrylate polymer particles was 20.0% by mass based on the total mass of the small-diameter (meth)acrylate polymer particles and the large-diameter (meth)acrylate polymer particles.

The proportion of the polymerization initiator to the (meth)acrylate monomer was 5.000% by mass, and the proportion of the polymerization accelerator to the (meth)acrylate monomer was 1.000% by mass.

With respect to the resultant bone cement composition kit (8), the doughing time was confirmed and the setting time was calculated out, by the same method as in Example 1. The results are shown in Table 1.

Example 9

A bone cement composition kit (hereinafter also referred to as "the bone cement composition kit (9)") was prepared in the same manner as in Example 1 except that none of titanium dioxide particles were used in Example 1, polymethyl methacrylate powder (product of SEKISUI PLASTICS CO., LTD.), whose average particle diameter was 30.00 µm, whose weight-average molecular weight was 135,000, and whose particle shape was spherical, was used as the large-diameter (meth)acrylate polymer particles in Example 1, and the used amounts of the large-diameter (meth)acrylate polymer particles, the small-diameter (meth)acrylate polymer particles, methyl methacrylate and N,N-dimethyl-p-toluidine were changed to 63.425% by mass, 3.338% by mass, 31.419% by mass and 0.344% by mass, respectively.

In this bone cement composition kit (9), the content of the large-diameter (meth)acrylate polymer particles was 64.599% by mass based on the total mass of the base-forming component, and the content of the small-diameter (meth)acrylate polymer particles was 5.0% by mass based on the total mass of the small-diameter (meth)acrylate polymer particles and the large-diameter (meth)acrylate polymer particles.

The proportion of the polymerization initiator to the (meth)acrylate monomer was 4.691% by mass, and the proportion of the polymerization accelerator to the (meth)acrylate monomer was 1.095% by mass.

With respect to the resultant bone cement composition kit (9), the doughing time was confirmed and the setting time was calculated out, by the same method as in Example 1. The results are shown in Table 1.

Example 10

A bone cement composition kit (hereinafter also referred to as "the bone cement composition kit (10)") was prepared in the same manner as in Example 9 except that the used amounts of the large-diameter (meth)acrylate polymer particles and the small-diameter (meth)acrylate polymer particles in Example 9 were changed to 60.087% by mass and 6.676% by mass, respectively.

In this bone cement composition kit (10), the content of the large-diameter (meth)acrylate polymer particles was 61.200% by mass based on the total mass of the base-forming component, and the content of the small-diameter (meth)acrylate polymer particles was 10.0% by mass based on the total mass of the small-diameter (meth)acrylate polymer particles and the large-diameter (meth)acrylate polymer particles.

With respect to the resultant bone cement composition kit (10), the doughing time was confirmed and the setting time was calculated out, by the same method as in Example 1. The results are shown in Table 1.

Example 11

A bone cement composition kit (hereinafter also referred to as "the bone cement composition kit (11)") was prepared in the same manner as in Example 9 except that the small-diameter (meth)acrylate polymer particles in Example 9 were changed to aggregates (particle shape: spherical) having an average particle diameter of 40 µm by means of a spray drying machine before use.

With respect to the resultant bone cement composition kit (11), the doughing time was confirmed and the setting time was calculated out, by the same method as in Example 1. The results are shown in Table 1.

Example 12

A bone cement composition kit (hereinafter also referred to as "the bone cement composition kit (12)") was prepared in the same manner as in Example 10 except that the small-diameter (meth)acrylate polymer particles in Example 10 were changed to aggregates having an average particle diameter of 40 µm by means of a spray drying machine before use.

With respect to the resultant bone cement composition kit (12), the doughing time was confirmed and the setting time was calculated out, by the same method as in Example 1. The results are shown in Table 1.

Example 13

A bone cement composition kit (hereinafter also referred to as "the bone cement composition kit (13)") was prepared in the same manner as in Example 3 except that polymethyl methacrylate-styrene copolymer powder (product of SEKISUI PLASTICS CO., LTD.), whose average particle diameter was 40.46 µm, whose weight-average molecular weight was 154,700, and whose particle shape was spherical, was used as the large-diameter (meth)acrylate polymer particles in Example 3, the used amounts of the large-diameter (meth)acrylate polymer particles and the small-diameter (meth)acrylate polymer particles were changed to 43.867% by mass and 7.440% by mass, respectively, the titanium dioxide particles (c) were used as the filler in place of the titanium dioxide particles (a), the used amount thereof was changed to 19.646% by mass, the used amount of benzoyl peroxide was changed to 1.473% by mass, the used amount of methyl methacrylate was changed to 27.279% by mass, and the used amount of N,N-dimethyl-p-toluidine was changed to 0.295% by mass.

In this bone cement composition kit (13), the content of the large-diameter (meth)acrylate polymer particles was 55.820% by mass based on the total mass of the base-forming component, and the content of the small-diameter (meth)acrylate polymer particles was 14.5% by mass based on the total mass of the small-diameter (meth)acrylate polymer particles and the large-diameter (meth)acrylate polymer particles.

The proportion of the polymerization initiator to the (meth)acrylate monomer was 5.400% by mass, and the proportion of the polymerization accelerator to the (meth)acrylate monomer was 1.081% by mass.

With respect to the resultant bone cement composition kit (13), the doughing time was confirmed and the setting time was calculated out, by the same method as in Example 1. The results are shown in Table 1.

Example 14

A bone cement composition kit (hereinafter also referred to as "the bone cement composition kit (14)") was prepared in the same manner as in Example 13 except that the used amounts of the large-diameter (meth)acrylate polymer particles and the small-diameter (meth)acrylate polymer particles in Example 13 were changed to 35.904% by mass and 6.336% by mass, respectively, 19.646% by mass of the titanium dioxide particles (c) and 9.823% by mass of barium sulfate were used as the filler, and the used amount of methyl methacrylate was changed to 26.523% by mass.

In this bone cement composition kit (14), the content of the large-diameter (meth)acrylate polymer particles was 52.214% by mass based on the total mass of the base-forming component, and the content of the small-diameter (meth)acrylate polymer particles was 15.0% by mass based on the total mass of the small-diameter (meth)acrylate polymer particles and the large-diameter (meth)acrylate polymer particles.

The proportion of the polymerization initiator to the (meth)acrylate monomer was 5.554% by mass, and the proportion of the polymerization accelerator to the (meth)acrylate monomer was 1.112% by mass.

With respect to the resultant bone cement composition kit (14), the doughing time was confirmed and the setting time was calculated out, by the same method as in Example 1. The results are shown in Table 1.

Example 15

A bone cement composition kit (hereinafter also referred to as "the bone cement composition kit (15)") was prepared in the same manner as in Example 14 except that the used amounts of the large-diameter (meth)acrylate polymer particles, the small-diameter (meth)acrylate polymer particles, barium sulfate and methyl methacrylate in Example 14 were changed to 32.181% by mass, 6.130% by mass, 14.735% by mass and 25.540% by mass, respectively.

In this bone cement composition kit (15), the content of the large-diameter (meth)acrylate polymer particles was 50.400% by mass based on the total mass of the base-forming component, and the content of the small-diameter (meth)acrylate polymer particles was 16.0% by mass based on the total mass of the small-diameter (meth)acrylate polymer particles and the large-diameter (meth)acrylate polymer particles.

The proportion of the polymerization initiator to the (meth)acrylate monomer was 5.767% by mass, and the proportion of the polymerization accelerator to the (meth)acrylate monomer was 1.155% by mass.

With respect to the resultant bone cement composition kit (15), the doughing time was confirmed and the setting time was calculated out, by the same method as in Example 1. The results are shown in Table 1.

Example 16

A bone cement composition kit (hereinafter also referred to as "the bone cement composition kit (16)") was prepared in the same manner as in Example 14 except that the used amounts of the large-diameter (meth)acrylate polymer particles, the small-diameter (meth)acrylate polymer particles, barium sulfate and methyl methacrylate in Example 14 were changed to 28.536% by mass, 5.846% by mass, 19.646% by mass and 24.558% by mass, respectively.

In this bone cement composition kit (16), the content of the large-diameter (meth)acrylate polymer particles was 48.415% by mass based on the total mass of the base-forming component, and the content of the small-diameter (meth)acrylate polymer particles was 17.0% by mass based on the total mass of the small-diameter (meth)acrylate polymer particles and the large-diameter (meth)acrylate polymer particles.

The proportion of the polymerization initiator to the (meth)acrylate monomer was 5.998% by mass, and the proportion of the polymerization accelerator to the (meth)acrylate monomer was 1.201% by mass.

With respect to the resultant bone cement composition kit (16), the doughing time was confirmed and the setting time was calculated out, by the same method as in Example 1. The results are shown in Table 1.

Example 17

A bone cement composition kit (hereinafter also referred to as "the bone cement composition kit (17)") was prepared in the same manner as in Example 14 except that zirconium oxide was used in place of barium sulfate in Example 14.

With respect to the resultant bone cement composition kit (17), the doughing time was confirmed and the setting time was calculated out, by the same method as in Example 1. The results are shown in Table 1.

Example 18

A bone cement composition kit (hereinafter also referred to as "the bone cement composition kit (18)") was prepared in the same manner as in Example 15 except that zirconium oxide was used in place of barium sulfate in Example 15.

With respect to the resultant bone cement composition kit (18), the doughing time was confirmed and the setting time was calculated out, by the same method as in Example 1. The results are shown in Table 1.

Example 19

A bone cement composition kit (hereinafter also referred to as "the bone cement composition kit (19)") was prepared in the same manner as in Example 16 except that zirconium oxide was used in place of barium sulfate in Example 16.

With respect to the resultant bone cement composition kit (19), the doughing time was confirmed and the setting time was calculated out, by the same method as in Example 1. The results are shown in Table 1.

Comparative Example 1

A bone cement composition kit (hereinafter also referred to as "the comparative bone cement composition kit (1)") was prepared in the same manner as in Example 1 except that the used amount of the large-diameter (meth)acrylate polymer particles in Example 1 was changed to 51.592% by mass, and the small-diameter (meth)acrylate polymer particles were not used.

In this comparative bone cement composition kit (1), the content of the large-diameter (meth)acrylate polymer particles was 65.625% by mass based on the total mass of the base-forming component.

With respect to the resultant comparative bone cement composition kit (1), the doughing time was and the setting time was calculated out, confirmed by the same method as in Example 1. The results are shown in Table 1.

Comparative Example 2

A bone cement composition kit (hereinafter also referred to as "the comparative bone cement composition kit (2)") was prepared in the same manner as in Example 1 except that polymethyl methacrylate powder having an average particle diameter of 4.0 μm was used in place of the small-diameter (meth)acrylate polymer particles in Example 1.

With respect to the resultant comparative bone cement composition kit (2), the doughing time was confirmed and the setting time was calculated out, by the same method as in Example 1. The results are shown in Table 1.

Comparative Example 3

A bone cement composition kit (hereinafter also referred to as "the comparative bone cement composition kit (3)") was prepared in the same manner as in Example 2 except that the used amount of the large-diameter (meth)acrylate polymer particles in Example 2 was changed to 51.592% by mass, and the small-diameter (meth)acrylate polymer particles were not used.

In this comparative bone cement composition kit (3), the content of the large-diameter (meth)acrylate polymer particles was 65.625% by mass based on the total mass of the base-forming component.

With respect to the resultant comparative bone cement composition kit (3), the doughing time was confirmed and the setting time was calculated out, by the same method as in Example 1. The results are shown in Table 1.

Comparative Example 4

A bone cement composition kit (hereinafter also referred to as "the comparative bone cement composition kit (4)") was prepared in the same manner as in Example 2 except that polymethyl methacrylate powder having an average particle diameter of 4.0 μm was used in place of the small-diameter (meth)acrylate polymer particles in Example 2.

With respect to the resultant comparative bone cement composition kit (4), the doughing time was confirmed and the setting time was calculated out, by the same method as in Example 1. The results are shown in Table 1.

Comparative Example 5

A bone cement composition kit (hereinafter also referred to as "the comparative bone cement composition kit (5)") was prepared in the same manner as in Example 7 except that the used amount of the large-diameter (meth)acrylate polymer particles in Example 7 was changed to 35.364% by mass, and the small-diameter (meth)acrylate polymer particles were not used.

In this comparative bone cement composition kit (5), the content of the large-diameter (meth)acrylate polymer particles was 60.001% by mass based on the total mass of the base-forming component.

With respect to the resultant comparative bone cement composition kit (5), the doughing time was confirmed and the setting time was calculated out, by the same method as in Example 1. The results are shown in Table 1.

Comparative Example 6

A bone cement composition kit (hereinafter also referred to as "the comparative bone cement composition kit (6)") was prepared in the same manner as in Example 8 except that the used amount of the large-diameter (meth)acrylate polymer particles in Example 8 was changed to 29.470% by mass, and the small-diameter (meth)acrylate polymer particles were not used.

In this comparative bone cement composition kit (6), the content of the large-diameter (meth)acrylate polymer particles was 50.000% by mass based on the total mass of the base-forming component.

With respect to the resultant comparative bone cement composition kit (6), the doughing time was confirmed and the setting time was calculated out, by the same method as in Example 1. The results are shown in Table 1.

TABLE 1

| | Large-diameter (meth)acrylate polymer particle | | | | Small-diameter (meth)acrylate polymer particle | | |
| | Large-diameter PMMA particle | | Large-diameter MMA/Sty. particle | | Small-diameter PMMA particle | | |
| | Average diameter (μm) | Content (wt %) | Average diameter (μm) | Content (wt %) | Average diameter (μm) | Content (wt %) | form |
|---|---|---|---|---|---|---|---|
| Example 1 | 39.77 | 57.094 | — | — | 0.5 | 13.0 | Primary particle |
| Example 2 | 33.93 | 57.750 | — | — | 0.5 | 12.0 | Primary particle |
| Example 3 | 39.77 | 57.094 | — | — | 0.5 | 13.0 | Aggregates having an average particle diameter of 40 μm |
| Example 4 | 33.93 | 57.750 | — | — | 0.5 | 12.0 | Aggregates having an average particle diameter of 40 μm |
| Example 5 | 45.58 | 56.438 | — | — | 0.5 | 14.0 | Primary particle |
| Example 6 | 45.58 | 56.438 | — | — | 0.5 | 14.0 | Aggregates having an average particle diameter of 40 μm |

TABLE 1-continued

| Example | | | | | | | |
|---|---|---|---|---|---|---|---|
| Example 7 | 31.11 | 51.000 | — | — | 0.5 | 15.0 | Aggregates having an average particle diameter of 40 μm |
| Example 8 | 12.93 | 39.999 | — | — | 0.5 | 20.0 | Aggregates having an average particle diameter of 40 μm |
| Example 9 | 30.00 | 64.599 | — | — | 0.5 | 5.0 | Primary particle |
| Example 10 | 30.00 | 61.200 | — | — | 0.5 | 10.0 | Primary particle |
| Example 11 | 30.00 | 64.599 | — | — | 0.5 | 5.0 | Aggregates having an average particle diameter of 40 μm |
| Example 12 | 30.00 | 61.200 | — | — | 0.5 | 10.0 | Aggregates having an average particle diameter of 40 μm |
| Example 13 | — | — | 40.46 | 55.820 | 0.5 | 14.5 | Aggregates having an average particle diameter of 40 μm |
| Example 14 | — | — | 40.46 | 52.214 | 0.5 | 15.0 | Aggregates having an average particle diameter of 40 μm |
| Example 15 | — | — | 40.46 | 50.400 | 0.5 | 16.0 | Aggregates having an average particle diameter of 40 μm |
| Example 16 | — | — | 40.46 | 48.415 | 0.5 | 17.0 | Aggregates having an average particle diameter of 40 μm |
| Example 17 | — | — | 40.46 | 52.214 | 0.5 | 15.0 | Aggregates having an average particle diameter of 40 μm |
| Example 18 | — | — | 40.46 | 50.400 | 0.5 | 16.0 | Aggregates having an average particle diameter of 40 μm |
| Example 19 | — | — | 40.46 | 48.415 | 0.5 | 17.0 | Aggregates having an average particle diameter of 40 μm |
| Comparative Example 1 | 39.77 | 65.625 | | | | 0 | — |
| Comparative Example 2 | 39.77 | 57.094 | | | | 4.0 | 13.0 Primary particle |
| Comparative Example 3 | 33.93 | 65.625 | | | | | 0 — |
| Comparative Example 4 | 33.93 | 57.750 | | | | 4.0 | 12.0 Primary particle |
| Comparative Example 5 | 31.11 | 60.001 | | | | | 0 — |
| Comparative Example 6 | 12.93 | 50.000 | | | | | 0 — |

| | Filler | | | | | |
|---|---|---|---|---|---|---|
| | Titanium dioxide particle | | Barium sulfate Content (wt %) | Zirconium oxide Content (wt %) | Doughing time (min) | Setting time (min) |
| | Median diameter (μm) | Content (wt %) | | | | |
| Example 1 | 2.7 | 19.654 | — | — | 4.50 | 11.48 |
| Example 2 | 2.7 | 19.654 | — | — | 4.50 | 10.20 |
| Example 3 | 2.7 | 19.654 | — | — | 3.75 | 11.45 |
| Example 4 | 2.7 | 19.654 | — | — | 3.50 | 10.15 |
| Example 5 | 2.7 | 19.654 | — | — | 4.75 | 11.90 |
| Example 6 | 2.7 | 19.654 | — | — | 3.50 | 11.37 |
| Example 7 | 3.1 | 39.293 | — | — | 3.75 | 9.20 |
| Example 8 | 3.1 | 39.293 | — | — | 3.75 | 10.27 |
| Example 9 | — | 0 | — | — | 3.75 | 8.07 |
| Example 10 | — | 0 | — | — | 3.00 | 8.07 |
| Example 11 | — | 0 | — | — | 3.50 | 7.48 |
| Example 12 | — | 0 | — | — | 2.75 | 7.68 |
| Example 13 | 2.9 | 19.646 | — | — | 2.75 | 9.63 |
| Example 14 | 2.9 | 19.646 | 9.823 | — | 3.25 | 10.55 |
| Example 15 | 2.9 | 19.646 | 14.735 | — | 3.25 | 10.48 |
| Example 16 | 2.9 | 19.646 | 19.646 | — | 3.50 | 10.50 |
| Example 17 | 2.9 | 19.646 | — | 9.623 | 3.25 | 10.27 |
| Example 18 | 2.9 | 19.646 | — | 14.735 | 3.25 | 10.18 |
| Example 19 | 2.9 | 19.646 | — | 19.646 | 3.25 | 10.48 |
| Comparative Example 1 | 2.7 | 19.654 | — | — | 7.50 | 10.62 |
| Comparative Example 2 | 2.7 | 19.654 | — | — | 6.75 | 10.73 |
| Comparative Example 3 | 2.7 | 19.654 | — | — | 6.75 | 9.55 |
| Comparative Example 4 | 2.7 | 19.654 | — | — | 6.25 | 9.98 |
| Comparative Example 5 | 3.1 | 39.293 | — | — | 8.00 | 13.35 |
| Comparative Example 6 | 3.1 | 39.293 | — | — | 7.50 | 11.63 |

In Table 1, "Large-diameter PMMA particle" means polymethyl methacrylate powder used in the preparation of each bone cement composition kit and indicates powder having a larger particle diameter when two kinds of polymethyl methacrylate powders different in particle diameter were used in the preparation of the composition kit, and "Content of large-diameter PMMA particle" indicates a proportion to the total mass of the base-forming component in the composition. "Large-diameter MMA/Sty. particle" indicates polymethyl methacrylate-styrene copolymer powder used in the preparation of each bone cement composition kit, and "Content of large-diameter MMA/Sty. particle" indicates a proportion to the total mass of the base-forming component in the composition. "Small-diameter PMMA particle" means polymethyl methacrylate powder used in the preparation of each bone cement composition kit and indicates powder having a smaller particle diameter when two kinds of polymethyl methacrylate powders different in particle diameter were used in the preparation of the composition kit, and "Content of small-diameter PMMA particle" indicates a proportion to the total mass of the small-diameter PMMA particles and the large-diameter (meth)acrylate polymer particles.

From the results described above, it is apparent that the doughing time is shortened within a range of 2.5 to 5 minutes according to the bone cement compositions of Example 1 to Example 19.

It is also apparent from comparison between Example 3 and Example 1, Example 4 and Example 2, Example 6 and Example 5, Example 11 and Example 9, and Example 12 and Example 10 that the doughing time is more shortened in the compositions that the small-diameter (meth)acrylate polymer particles are contained as aggregates than the compositions that the small-diameter (meth)acrylate polymer particles are contained as primary particles, not as aggregates.

On the other hand, it was confirmed that the bone cement compositions of Comparative Example 1, Comparative Example 3, Comparative Example 5 and Comparative Example 6 require the doughing time of at least 5 minutes because the small-diameter (meth)acrylate polymer particles are not contained. It is also apparent that the bone cement compositions of Comparative Example 2 and Comparative Example 4 require the doughing time of at least 5 minutes because the average particle diameter of the small-diameter polymer particles is too large as 4 µm though two kinds of (meth)acrylate polymer particles different in average particle diameter were contained.

In addition, in the bone cement compositions of Example 1 to Example 19, it is apparent that improvement in workability attending on extension of the working time (specifically, that is a time up to setting from after the passage of the doughing time and means a time obtained by subtracting "doughing time" from "setting time (a time up to setting from the beginning of kneading)" is expected.

It was further confirmed that according to the compositions of Example 1 to Example 8, and Example 13 to Example 19, excellent bioactivity is achieved because the titanium dioxide particles are contained. In particular, in the compositions of Example 14 to Example 19, it was confirmed from the observation of a surface of a bone cement hardened material obtained from each composition and its surface after immersed in a simulated body fluid for 14 days under condition of 36.5° C. in temperature through an electron microscope (SEM) that the addition of zirconium oxide or barium sulfate does not cause the manifestation of the bioactivity derived from the titanium dioxide particles to incur an evil even when zirconium oxide or barium sulfate is contained together with the titanium dioxide particles as a filler. Specifically, as illustrated in FIG. 1 to FIG. 8, the formation of hydroxyapatite (indicated by a character of "HAp" in each drawing) was observed at the surfaces after immersed in the simulated body fluid even in the bone cement hardened materials obtained from the compositions of Example 14 to Example 19 like the bone cement hardened material obtained from the composition of Example 13 containing only the titanium dioxide particle as a filler.

Figure 2:
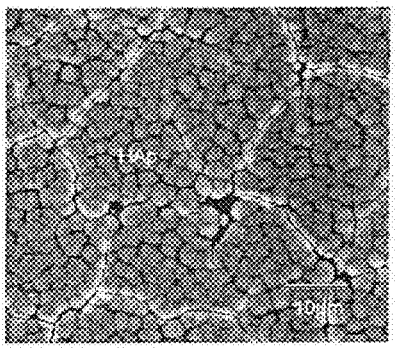
FIG. 2 illustrates an SEM photograph showing a surface after soaking in the simulated body fluid of the bone cement hardened material obtained from the composition of Example 13.
Figure 3:
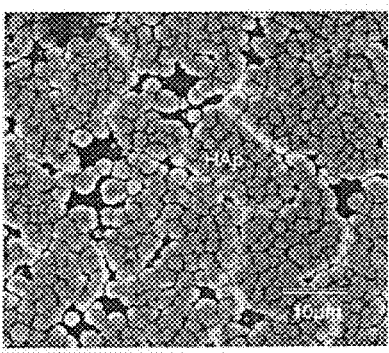
FIG. 3 illustrates an SEM photograph showing a surface after soaking in the simulated body fluid of a bone cement hardened material obtained from a composition of Example 14.
Figure 4:
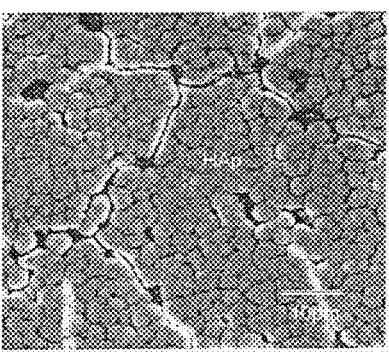
FIG. 4 illustrates an SEM photograph showing a surface after soaking in the simulated body fluid of a bone cement hardened material obtained from a composition of Example 15.
Figure 5:
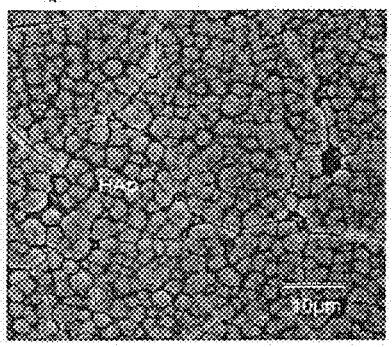
FIG. 5 illustrates an SEM photograph showing a surface after soaking in the simulated body fluid of a bone cement hardened material obtained from a composition of Example 16.
Figure 6:
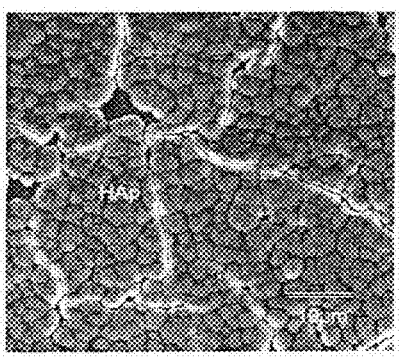
FIG. 6 illustrates an SEM photograph showing a surface after soaking in the simulated body fluid of a bone cement hardened material obtained from a composition of Example 17.
Figure 7:
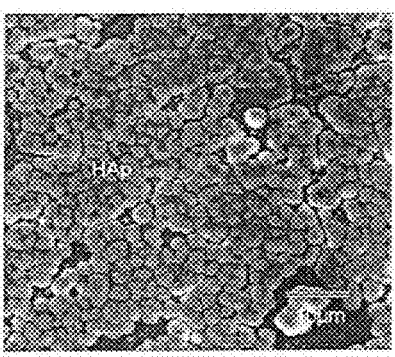
FIG. 7 illustrates an SEM photograph showing a surface after soaking in the simulated body fluid of a bone cement hardened material obtained from a composition of Example 18.
Figure 8:
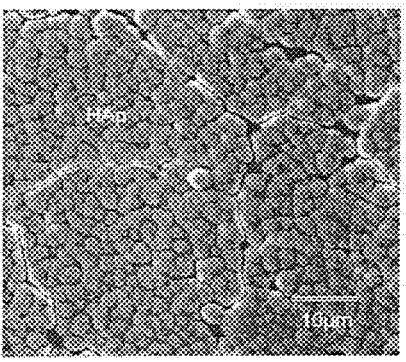
FIG. 8 illustrates an SEM photograph showing a surface after soaking in the simulated body fluid of a bone cement hardened material obtained from a composition of Example 19.

Here, FIG. 1 illustrates an SEM photograph showing a surface (before immersed in the simulated body fluid) of the bone cement hardened material obtained from the composition of Example 13. FIG. 2 illustrates an SEM photograph showing a surface after immersed in the simulated body fluid of the bone cement hardened material obtained from the composition of Example 13. FIG. 3 to FIG. 8 respectively illustrate SEM photographs showing surfaces after immersed in the simulated body fluid of the bone cement hardened materials obtained from the compositions of Example 14 to Example 19.

Figure 9:
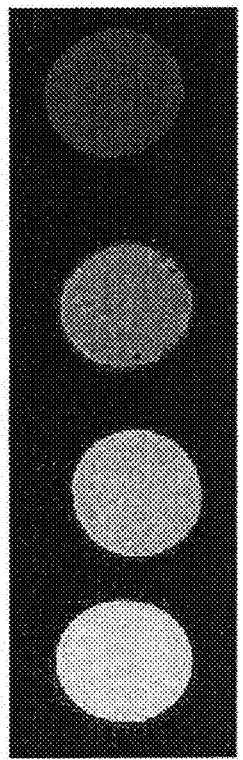
FIG. 9 illustrates photographs of the bone cement hardened materials obtained from the compositions of Example 13 to Example 16, said photographs being obtained by determination of radiopacity, and a photograph in Example 13, a photograph in Example 14, a photograph in Example 15 and a photograph in Example 16 in order from above.
Figure 10:
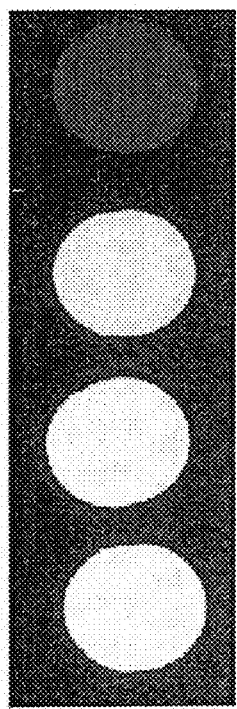
FIG. 10 illustrates photographs of the bone cement hardened materials obtained from the compositions of Example 13, and Example 17 to Example 19, said photographs being obtained by determination of radiopacity, and the photograph in Example 13, a photograph in Example 17, a photograph in Example 18 and a photograph in Example 19 in order from above.

In addition, according to the compositions of Example 14 to Example 19, excellent radiopacity is achieved as apparent from the results shown in FIG. 9 and FIG. 10 obtained by the following determination of radiopacity because zirconium oxide or barium sulfate is contained. It was confirmed that the radiopacity becomes higher as the amount of zirconium oxide or barium sulfate added increases.

Here, FIG. 9 illustrates photographs of the bone cement hardened material obtained from the composition ($TiO_2$: 19.646% by mass, $BaSO_4$: 0% by mass) of Example 13, the bone cement hardened material obtained from the composition ($TiO_2$: 19.646% by mass, $BaSO_4$: 9.823% by mass) of Example 14, the bone cement hardened material obtained from the composition ($TiO_2$: 19.646% by mass, $BaSO_4$: 14.735% by mass) of Example 15 and the bone cement hardened material obtained from the composition ($TiO_2$: 19.646% by mass, $BaSO_4$: 19.646% by mass) of Example 16 in order from above, and the photographs are arranged in such a manner that the content of barium sulfate increases toward below from above. FIG. 10 illustrates photographs of the bone cement hardened material obtained from the composition ($TiO_2$: 19.646% by mass, $ZrO_2$: 0% by mass) of Example 13, the bone cement hardened material obtained from the composition ($TiO_2$: 19.646% by mass, $ZrO_2$: 9.823% by mass) of Example 17, the bone cement hardened material obtained from the composition ($TiO_2$: 19.646% by mass, $ZrO_2$: 14.735% by mass) of Example 18 and the bone cement hardened material obtained from the composition ($TiO_2$: 19.646% by mass, $ZrO_2$: 19.646% by mass) of Example 19 in order from above, and the photographs are arranged in such a manner that the content of zirconium oxide increases toward below from above.

[Determination of Radiopacity]

With respect to the bone cement hardened material obtained from each bone cement composition, a specimen having a diameter of 15 mm and a thickness of 5 mm was provided, and this specimen of the bone cement hardened material was photographed under conditions of a tube voltage of 42 kV and a photographing current-time product of 1.60 mAs by means of "Radiographic Machine for Exclusive Use of Small Animals, VPX-40B"(manufactured by TOSHIBA MEDICAL SUPPLY CO., LTD.) using "Medical Film SRD" (product of KONICA MINOLTA HOLDINGS, INC.) as a film. Thereafter, the radiopacity thereof was confirmed on the basis of a photograph obtained by developing the film by means of "Automatic Developer AP500" (manufactured by DAITO CO., LTD.).

The invention claimed is:

1. A bone cement composition comprising:
large-diameter (meth)acrylate polymer particles having an average particle diameter of 10 to 60 μm;
small-diameter (meth)acrylate polymer particles having an average particle diameter of 0.1 to 2.0 μm;
a (meth)acrylate monomer; and
a polymerization initiator,
wherein the content of the small-diameter (meth)acrylate polymer particles is 5 to 30% by mass based on a total mass of the small-diameter (meth)acrylate polymer particles and the large-diameter (meth)acrylate polymer particles, and a part or a whole of the small-diameter (meth)acrylate polymer particles are contained in the form of aggregates having an average particle diameter of 30 to 50 μm.

2. The bone cement composition according to claim 1, further comprising a filler.

3. The bone cement composition according to claim 2, wherein the filler contains at least titanium dioxide particles.

4. The bone cement composition according to claim 3, wherein the titanium dioxide particles have a median diameter of 0.5 to 7.0 μm as measured by a laser diffraction/scattering particle size distribution analyzer and are spherical.

5. The bone cement composition according to claim 3, wherein the filler further contains at least one of barium sulfate and zirconium oxide.

6. A bone cement composition kit for obtaining the bone cement composition according to claim 1, comprising a polymerization initiator-containing kit component containing large-diameter (meth)acrylate polymer particles, small-diameter (meth)acrylate polymer particles and a polymerization initiator, and a monomer-containing kit component containing a (meth)acrylate monomer, wherein a part or a whole of the small-diameter (meth)acrylate polymer particles are contained in the form of aggregates having an average particle diameter of 30 to 50 μm.

7. The bone cement composition kit according to claim 6, wherein the polymerization initiator-containing kit component contains a filler containing at least titanium dioxide particles.

8. A production method of a bone cement hardened material, comprising:
a step of kneading a (meth)acrylate monomer and a polymerization initiator in the presence of large-diameter (meth)acrylate polymer particles having an average particle diameter of 10 to 60 μm and small-diameter (meth)acrylate polymer particles having an average particle diameter of 0.1 to 2.0 μm to polymerize the (meth)acrylate monomer,
wherein the small-diameter (meth)acrylate polymer particles are used in a proportion of 5 to 30% by mass based on a total mass of the small-diameter (meth)acrylate polymer particles and the large-diameter (meth)acrylate polymer particles.

9. The production method of the bone cement hardened material according to claim 8, wherein the (meth)acrylate monomer is polymerized by performing a process of leaving the kneaded product of the (meth)acrylate monomer and the polymerization initiator to stand.

10. The production method of the bone cement hardened material according to claim 8, wherein the kneading of the (meth)acrylate monomer and the polymerization initiator is conducted in the presence of a filler containing at least titanium dioxide particles together with the large-diameter (meth)acrylate polymer particles and the small-diameter (meth)acrylate polymer particles.

11. The production method of the bone cement hardened material according to claim 8, wherein a part or a whole of the small-diameter (meth)acrylate polymer particles are kneaded in the form of aggregates having an average particle diameter of 30 to 50 μm.

* * * * *